US010516866B2

(12) United States Patent
Fukunaga

(10) Patent No.: US 10,516,866 B2
(45) Date of Patent: Dec. 24, 2019

(54) IMAGING DEVICE AND ENDOSCOPE DEVICE

(71) Applicant: OLYMPUS CORPORATION, Hachioji-shi, Tokyo (JP)

(72) Inventor: Yasuhiro Fukunaga, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 2 days.

(21) Appl. No.: 15/912,991

(22) Filed: Mar. 6, 2018

(65) Prior Publication Data

US 2018/0199018 A1 Jul. 12, 2018

Related U.S. Application Data

(63) Continuation of application No. PCT/JP2015/080229, filed on Oct. 27, 2015.

(51) Int. Cl.
*H04N 9/00* (2006.01)
*A61B 1/00* (2006.01)
(Continued)

(52) U.S. Cl.
CPC ......... *H04N 9/646* (2013.01); *A61B 1/00009* (2013.01); *A61B 1/00163* (2013.01);
(Continued)

(58) Field of Classification Search
CPC .... H04N 9/606; H04N 9/646; H04N 9/04557; A61B 1/00009; A61B 1/00186
(Continued)

(56) References Cited

U.S. PATENT DOCUMENTS

2007/0084986 A1* 4/2007 Yang ................. H01L 27/14603
250/208.1
2016/0256039 A1* 9/2016 Fukunaga ......... H01L 27/14621

FOREIGN PATENT DOCUMENTS

JP 2008-216479 A 9/2008
JP 2010-135700 A 6/2010
(Continued)

OTHER PUBLICATIONS

International Search Report dated Jan. 19, 2016, issued in counterpart International Application No. PCT/JP2015/080229, w/English translation (3 pages).
(Continued)

*Primary Examiner* — Jeffery A Williams
(74) *Attorney, Agent, or Firm* — Westerman, Hattori, Daniels & Adrian, LLP

(57) ABSTRACT

An imaging device includes a first substrate with a pixel array having a plurality of first pixels; a second substrate stacked with the first substrate on a side opposite to a light-receiving surface of the pixel array; a filter for narrowing a band of light of a first wavelength; and a plurality of second pixels included in the second substrate for receiving light whose band is narrowed by the filter, wherein the filter configured by a first Fabry-Perot filter or a second Fabry-Perot filter, the first Fabry-Perot filter and the second Fabry-Perot filter have different transmission wavelength bands, a peak wavelength of the transmission wavelength band of the first Fabry-Perot filter is narrow band light in the vicinity of 600 nm, and a peak wavelength of the transmission wavelength band of the second Fabry-Perot filter is narrow band light in the vicinity of 630 nm.

7 Claims, 15 Drawing Sheets

(51) Int. Cl.
*H04N 9/64* (2006.01)
*A61B 1/06* (2006.01)
*H04N 5/225* (2006.01)
*H04N 9/07* (2006.01)
*H04N 9/04* (2006.01)
*H04N 5/369* (2011.01)
*A61B 1/05* (2006.01)

(52) U.S. Cl.
CPC .......... *A61B 1/00186* (2013.01); *A61B 1/051* (2013.01); *A61B 1/0638* (2013.01); *A61B 1/0646* (2013.01); *H04N 5/2256* (2013.01); *H04N 5/2258* (2013.01); *H04N 5/379* (2018.08); *H04N 9/04555* (2018.08); *H04N 9/04557* (2018.08); *H04N 9/04561* (2018.08); *H04N 9/07* (2013.01); *H04N 2005/2255* (2013.01)

(58) Field of Classification Search
USPC .......................................................... 348/71
See application file for complete search history.

(56) References Cited

FOREIGN PATENT DOCUMENTS

| JP | 5355820 B2 | 11/2013 |
| JP | 2015-99875 A | 5/2015 |
| WO | 2013/145410 A1 | 10/2013 |

OTHER PUBLICATIONS

Office Action dated May 28, 2019, issued in counterpart JP application No. 2017-547228, with English translation. (4 pages).

* cited by examiner

IMAGING DEVICE AND ENDOSCOPE DEVICE

This application is a continuation application based on a PCT International Application No. PCT/JP2015/080229, filed on Oct. 27, 2015. The content of the PCT International Application is incorporated herein by reference.

BACKGROUND OF THE INVENTION

Field of the Invention

The present invention relates to an imaging device and an endoscope device.

Description of Related Art

In general, in a surgical, procedure in which a submucosal layer on which a lesion is present is incised and peeled while imaging is performed using an endoscope, a doctor checks positions of blood vessels and performs a treatment such as an incision such that a relatively thick blood vessel in the mucous membrane is not cut by an electric scalpel or the like.

Therefore, a technology capable of emitting light of three wavelengths of 540 nm, 600 nm, and 630 nm in addition to RGB and clearly imaging a thick blood vessel using an endoscope equipped with a rotation filter is known (for example, refer to Japanese Patent No. 5355820).

Light at 540 nm is effective for observing a shallow blood vessel. Light at 600 nm reaches the vicinity of a thick blood vessel deep in the submucosal layer, and light at 630 nm reaches a position deeper than the thick blood vessel. Therefore, it is possible to observe the thick blood vessel by using the light at 600 nm and 630 nm.

SUMMARY OF THE INVENTION

According to a first aspect of the present invention, an imaging device includes a first substrate which includes a pixel array having a plurality of first pixels; a second substrate which is disposed to be stacked with the first substrate on a side opposite to a light-receiving surface of the pixel array; a filter configured to narrow a band of light of a first wavelength to a predetermined wavelength band, the light of the first wavelength having passed through the first substrate; and a plurality of second pixels which are included in the second substrate, the plurality of second pixels receiving light whose band is narrowed by the filter, wherein the filter is configured by a first Fabry-Perot filter or a second Fabry-Perot filter according to a position of each of the second pixels, the first Fabry-Perot filter and the second Fabry-Perot filter have different transmission wavelength bands, a peak wavelength of the transmission wavelength band of the first Fabry-Perot filter is narrow band light in the vicinity of 600 nm, and a peak wavelength of the transmission wavelength band of the second Fabry-Perot filter is narrow band light in the vicinity of 630 nm.

According to a second aspect of the present invention, the imaging device according to the first aspect may further include a spectroscopic signal generation unit configured to generate a spectroscopic signal by using pixel signals output from the first pixels and the second pixels according to the light received by the first pixels and the second pixels, and the spectroscopic signal generation unit may generate a spectroscopic signal according to a difference between a pixel signal output from the first pixels and a pixel signal output from the second pixels, the spectroscopic signal being different from the pixel signals output from each of the first pixels and the second pixels.

According to a third aspect of the present invention, in the imaging device according to the first aspect, a peak wavelength of light whose band is narrowed by the filter may be in the vicinity of 630 nm.

According to a fourth aspect of the present invention, in the imaging device according to the first aspect, the first pixels may include an R pixel for detecting red light, a G pixel for detecting green light, or a B pixel for detecting blue light, and the filter and the second pixels may he arranged in the second substrate to receive light which has passed through the R pixel among the plurality of first pixels.

According to a fifth aspect of the present invention, the imaging device according to the first aspect may further include a second filter which narrows a band of light which has passed through a G pixel for detecting green light among the first pixels to a predetermined wavelength band; and a plurality of third pixels which are included in the second substrate and receive light whose band is narrowed by the second filter, wherein the first pixels may include an R pixel for detecting red light, a G pixel for detecting green light, and a B pixel for detecting blue light, and the second filter and the third pixels may be arranged in the second substrate to receive light which has passed through the G pixel among the plurality of first pixels.

According to a sixth aspect of the present invention, in the imaging device according to the first aspect, the first pixels may include a C pixel for detecting cyan light, an M pixel for detecting magenta light, and a Y pixel for detecting yellow light, and the filter and the second pixels may be arranged in the second substrate to receive light which has passed through the M pixel or the Y pixel among the plurality of first pixels.

According to a seventh aspect of the present invention, in the imaging device according to the first aspect, one or more first pixels may be clear pixels, and the filter and the second pixels may be arranged in the second substrate such that the filter and the second pixels receive light which has passed through the clear pixels among the plurality of first pixels.

According to an eighth aspect of the present invention, in the imaging device according to the first aspect, one or more first pixels may be pixels configured to detect narrow band light whose wavelength is in the vicinity of 540 nm.

According to a ninth aspect of the present invention, an endoscope device includes a light source configured to emit white illumination light to a subject; and an imaging device configured to image returning light of the illumination light emitted to the subject from the light source, wherein the imaging device includes a first substrate which includes a pixel array having a plurality of first pixels; a second substrate which is disposed to be stacked with the first substrate on a side opposite to a light-receiving surface of the pixel array; a filter configured to narrow a band of light of a first wavelength band to a predetermined wavelength band, the light of the first wavelength having passed through the first substrate; and a plurality of second pixels which are included in the second substrate and receive light whose band is narrowed by the filter, the filter is configured by a first Fabry-Perot filter or a second Fabry-Perot filter according to a position of each of the second pixels, the first Fabry-Perot filter and the second Fabry-Perot filter have different transmission wavelength bands, a peak wavelength of the transmission wavelength band of the first Fabry-Perot filter is narrow band light in the vicinity of 600 nm, and a peak wavelength of the transmission wavelength band of the second Fabry-Perot filter is narrow band light in the vicinity of 630 nm.

DETAILED DESCRIPTION OF THE INVENTION

Figure 1:
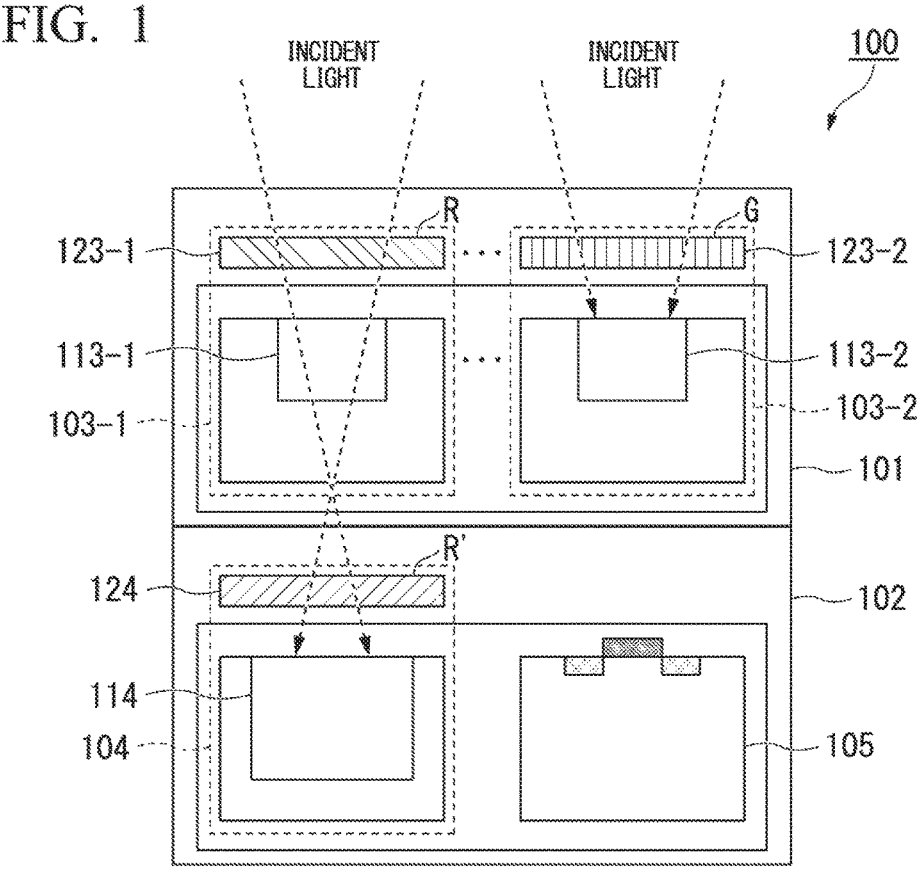
FIG 1 is a sectional diagram which shows a cross-section of on imaging element according to a first embodiment of the present invention.

Embodiments of the present invention will be described with reference to drawings.
(First Embodiment)
FIG. 1 is a sectional diagram which shows a cross-section of an imaging element 100 according to a first embodiment of the present invention. In the example shown, the imaging element 100 includes a first substrate 101, a second substrate 102, a plurality of first pixels 103 (pixel array), a plurality of second pixels 104, and a plurality of circuit portions 105. A side irradiated with incident light is set as a light-receiving surface.

The first substrate 101 and the second substrate 102 are stacked. The first substrate 101 and the second substrate 102 are silicon substrates. The first substrate 101 transmits a portion of incident light.

The first pixels 103 are arranged in the first substrate 101. A first pixel 103-1 among the first pixels 103 includes a first photodiode 113-1 for detecting light and a color filter 123-1 for transmitting light having a peak wavelength of 600 nm (red light). Accordingly, the first pixel 103-1 outputs a first signal (an R signal, a red signal) in accordance with an exposure amount of the light having a peak wavelength of 600 nm (red light) among the incident light. Hereinafter, the first pixel 103-1 is also referred to as an R pixel.

A first pixel 103-2 among the first pixels 103 includes a first photodiode 113-2 for detecting light and a color filter 123-2 for transmitting light having a peak wavelength of 540 nm (green light). Accordingly, the first pixel 103-2 outputs a second signal (a G signal, a green signal) in accordance with an exposure amount of the light, having a peak wavelength of 540 nm (green light) among the incident light. Hereinafter, the first pixel 103-2 is also referred to as a G pixel.

Although not shown in FIG. 1, a first pixel 103-3 among the first pixels 103 includes a first photodiode 113-3 for detecting light and a color filter 123-3 for transmitting light having a peak wavelength of 460 nm (blue light). Accordingly, the first pixel 103-3 outputs a third signal (a B signal, a blue signal) in accordance with an exposure amount of the light having a peak wavelength of 460 nm (blue light) among the incident light. Hereinafter, the first pixel 103-3 is also referred to as a B pixel.

The second pixels 104 are arranged in the second substrate 102. The second pixels 104 each include a second photodiode 114 for detecting light, and a color filter 124 for transmitting light having a peak wavelength of 630 nm (red light). Accordingly, the second pixels 104 each output a fourth signal (an R' signal, a red' signal) in accordance with an exposure amount of the light having a peak wavelength of 630 nm (red light) among the incident light. Hereinafter, the second pixels 104 are referred to as R' pixels. The circuit portions 105 include various types of circuits. Various types of circuits will be described below.

In the example shown, incident light is directly incident on the first pixels 103. On the other hand, incident light which has passed through the first substrate 101 is incident on the second pixels 104.

Figure 2:
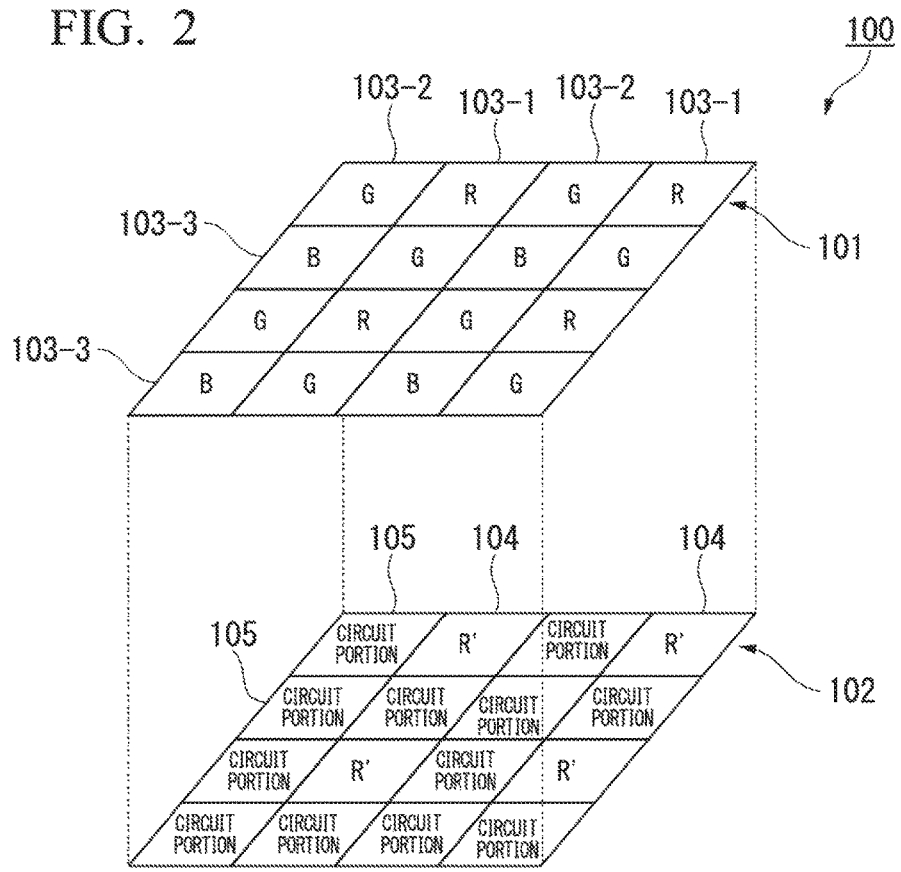
FIG. 2 is a schematic diagram which shows an arrangement of a first pixel, a second pixel, and a circuit portion according to the first embodiment of the present invention.

Next, an arrangement of the first pixels 103, the second pixels 104, and the circuit portions 105 will be described. FIG. 2 is a schematic diagram which shows the arrangement of the first pixels 103, the second pixels 104, and the circuit portions 105 in the present embodiment. In the example shown in FIG. 2, sixteen first pixels 103 regularly arranged in a two-dimensional shape of four rows and four columns are included in the first substrate 101. Four second pixels 104 and 12 circuit portions 105 regularly arranged in a two-dimensional shape of four rows and four columns are included in the second substrate 102.

As shown in FIG. 2, the first pixels 103-1 (R pixel), the first pixels 103-2 (G pixel), and the first pixels 103-3 (B pixel) are arranged in a Bayer arrangement in the first substrate 101. Incident light is directly incident on the first pixels 103-1 to 103-3. Therefore, it is possible to output a first signal (R signal) in accordance with an exposure amount of red light among the incident light, a second signal (G signal) in accordance with an exposure amount of green light among the incident light, and a third signal (B signal) in accordance with an exposure amount of blue light among the incident light in the first substrate 101.

As shown in FIG. 2, the second pixels 104 are arranged at positions corresponding to the first pixels 103-1 (for example, positions immediately under the first pixels 103-1) in the second substrate 102. Moreover, the circuit portions 105 are arranged at positions corresponding to the first pixels 103-2 to 103-3 (for example, positions immediately under the first pixels 103-2 to 103-3) in the second substrate 102.

With this arrangement, light which has passed through the first pixel 103-1 of the first substrate 101 is incident on the second pixel 104. A color filter 123-1 included in the first pixel 103-1 transmits the light having a peak wavelength of 600 nm (red light). The first substrate 101 is a silicon substrate, and transmits light in a wavelength band which includes a wavelength of red light. Therefore, the light having a peak wavelength of 600 nm (red light) among the incident light is incident on the second pixel 104 of the second substrate 102.

Therefore, even if the first pixel 103-1 of the first substrate 101 is present on a light-receiving surface side of the second pixel 104 of the second substrate 102, the second pixel 104 can output a fourth signal (an R' signal, a red' signal) in accordance with an exposure amount of light having a peak wavelength of 630 nm (red light) among the incident light.

The color filter 123-2 included in the first pixel 103-2 transmits only the light having a peak wavelength of 540 nm (green light). That is, the color filter 123-2 does not transmit red light. Moreover, the color filter 123-3 included in the first pixel 103-3 transmits only light having a peak wavelength of 460 nm (blue light). That is, the color filter 123-3 does not transmit red light. Therefore, light passing through the first pixels 103-2 and 103-3 does not include red light.

Accordingly, even if the second pixels 104 are arranged under the first pixels 103-2 and 103-3, it is difficult to accurately detect light having a peak wavelength of 630 nm (red light). For example, if various types of circuits are arranged around the first pixel 103 and the second pixel 104, it is considered that the aperture ratios of the first pixels 103 and the second pixels 104 decrease and the S/N ratios of the first to fourth signals decrease.

In the present embodiment, various types of circuits are arranged as the circuit portions 105 under the first pixel 103-2 (G pixel) and the first pixel 103-3 (B pixel) which do not easily transmit the light having a peak wavelength of 630 nm (red light), and thereby the aperture ratios of the first pixels 103-1 to 103-3 and the second pixel 104 can increase. Accordingly, it is possible to increase the S/N ratios of the first to third signals output by the first pixels 103-1 to 103-3. Moreover, it is possible to increase the S/N ratio of the fourth signal output by the second pixel. A light shielding layer may be provided between the first substrate 101 and the circuit portion 105 such that the circuit portion 105 is not irradiated with light.

The number and arrangement of the first pixels 103-1 to 103-3 included in the first substrate 101 and the second pixels 104 and the circuit portions 105 included in the second substrate 102 are not limited to the example shown in FIG. 2, and may be any number and arrangement. In the example shown in FIG. 2, the second pixels 104 are arranged under the first pixels 103-1 in a corresponding manner, but the present embodiment is not limited thereto. For example, it is possible to devise such a method that a pixel size of the second pixel 104 is set to a size different from a pixel size of the first pixel 103-1 (for example, an integral multiple of the first pixel 103-1). For example, it is possible to devise such a method that a size of the circuit portion 105 is set to a size different from a pixel size of the first pixel 103-2 or the first pixel 103-3.

Moreover, since the first pixels 103-1 to 103-3 and the second pixels 104 are irradiated with incident light at the same time due to the arrangement of the first pixels 103-1 to 103-3 and the second pixels 104 described above, it is possible to simultaneously output the first signal (R signal), the second signal (G signal), the third signal (B signal), and the fourth signal (R' signal). As a result, positional deviation can be prevented from occurring in an image of each wavelength.

Figure 3:
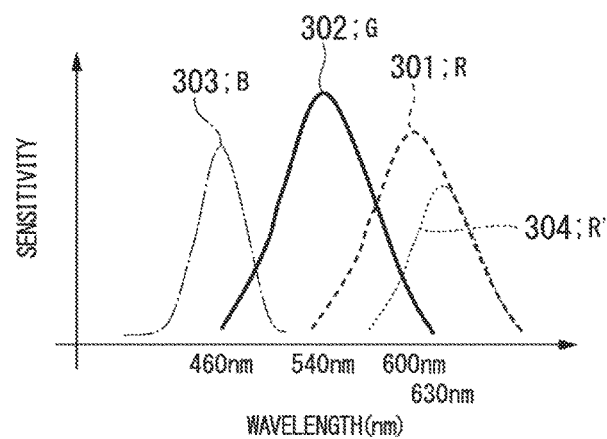
FIG. 3 is a graph which shows the sensitivity of the first pixel and the second pixel in the first embodiment of the present invention.

FIG. 3 is a graph which shows sensitivity of the first pixels 103-1 to 103-3 and the second pixel 104 in the present embodiment. The horizontal axis of the graph represents a wavelength (nm). The vertical axis of the graph represents the sensitivity of the first pixels 103-1 to 103-3 and the second pixel 104.

A line 301 is a line indicating the sensitivity of the first pixel 103-1 (R pixel). As shown in FIG. 3, the first pixel 103-1 (R pixel) has sensitivity in accordance with a wavelength band having a peak wavelength of 600 nm. A line 302 is a line indicating the sensitivity of the first pixel 103-2 (G pixel). As shown in FIG. 3, the first pixel 103-2 (G pixel) has sensitivity in accordance with a wavelength band having a peak wavelength of 540 nm.

A line 303 is a line indicating the sensitivity of the first pixel 103-3 (B pixel). As shown in FIG. 3, the first pixel 103-3 (B pixel) has the sensitivity in accordance with a wavelength band having a peak wavelength of 460 nm. A line 304 is a line indicating the sensitivity of the second pixel 104 (R' pixel). As shown in FIG. 3, the second pixel 104 (R' pixel) has the sensitivity in accordance with a wavelength band having a peak wavelength of 630 nm.

Figure 4:
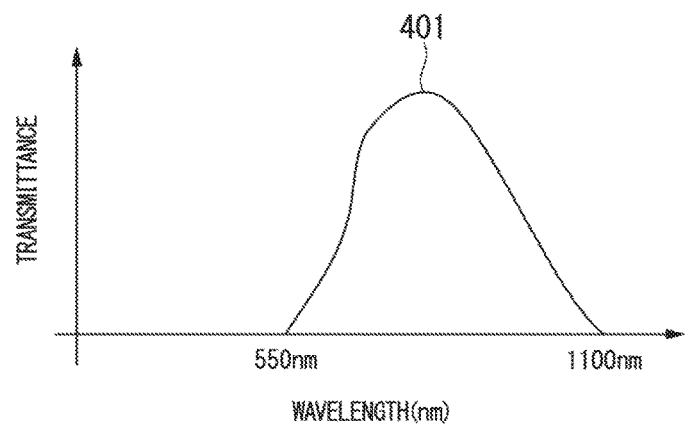
FIG. 4 is a graph which shows a transmittance of a silicon substrate in the first embodiment of the present invention.

FIG. 4 is a graph which shows a transmittance of a silicon substrate in the present embodiment. The horizontal axis of the graph represents a wavelength (nm). The vertical axis of the graph represents a transmittance of a silicon substrate.

A line 401 is a line indicating a transmittance of a silicon substrate. As shown in FIG. 3, the silicon substrate transmits light in a wavelength band of 500 nm to 1100 nm. In this manner, the silicon substrate transmits light in a wavelength including the wavelength of red light (for example, light in a wavelength band having a peak wavelength of 630 nm). Therefore, red light among the incident light passes through the first substrate 101 and is incident on the second substrate 102. Accordingly, even if the first substrate 101 and the second substrate 102 are stacked, the second pixel 104 of the second substrate 102 can output a fourth signal (an R' signal, a red' signal) in accordance with an exposure amount of the light (red light) having the peak wavelength of 630 nm among the incident light. As a result, a pixel (for example, the second pixel 104) for detecting long wavelength light can be used in the second substrate 102.

Figure 5:
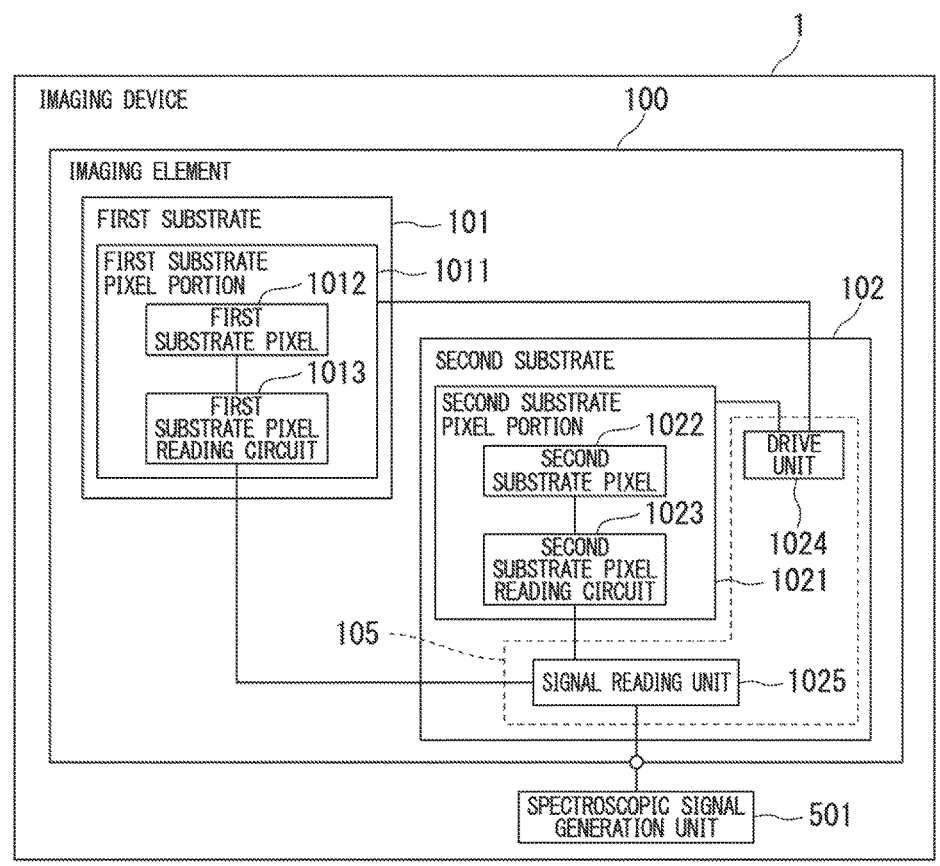
FIG. 5 is a block diagram which shows a configuration of an imaging device according to the first embodiment of the present invention.

Next, a configuration of the imaging device 1 will be described. FIG. 5 is a block diagram which shows a configuration of the imaging device 1 according to the present embodiment. The imaging device 1 includes the imaging element 100 and a spectroscopic signal generation unit 501. The imaging element 100 includes the first substrate 101 and the second substrate 102. The first substrate 101 includes a first substrate pixel portion 1011.

The first substrate pixel portion 1011 includes a first substrate pixel 1012 and a first substrate pixel reading circuit

1013. The first substrate pixel 1012 includes the plurality of first pixels 103 described above. The second substrate 102 includes a second substrate pixel portion 1021 and the plurality or circuit portions 105. The second substrate pixel portion 1021 includes a second substrate pixel 1022 and a second substrate pixel reading circuit 1023. The second substrate pixel 1022 includes the plurality of second pixels 104 described above.

The circuit portion 105 includes a drive unit 1024 and a signal reading unit 1025 as various types of circuits. The drive unit 1024 transmits a control signal, and drives the first substrate pixel portion 1011 and the second substrate pixel portion 1021. The signal reading unit 1025 includes a circuit for removing noise of a signal, a circuit for performing A/D conversion, and a scanning circuit. The signal reading unit 1025 controls the first substrate pixel reading circuit 1013, and reads the first to third signals from the first substrate pixel 1012. The signal reading unit 1025 controls the second substrate pixel reading circuit 1023, and reads the fourth signal from the second substrate pixel 1022. The first substrate pixel reading circuit 1013 and the second substrate pixel reading circuit 1023 may be disposed in the circuit portion 105.

The spectroscopic signal generation unit 501 generates a spectroscopic signal using the first to fourth signals read by the signal reading unit 1025, and generates an image. Specifically, the spectroscopic signal generation unit 5016 performs deraosaicing processing using the third signal (B signal) according to the second signal (G signal), a signal corresponding to a wavelength of 600 nm which is obtained by subtracting the fourth signal (R' signal) from the first signal (R signal), and a signal corresponding to a wavelength of 630 nm which is the fourth signal (R' signal). A wavelength image with wavelengths of λ1 corresponding to a wavelength of the G signal, λ2 corresponding to a wavelength of the R signal—the R' signal, and λ3 corresponding to a wavelength of the R' signal is generated.

Figure 6:
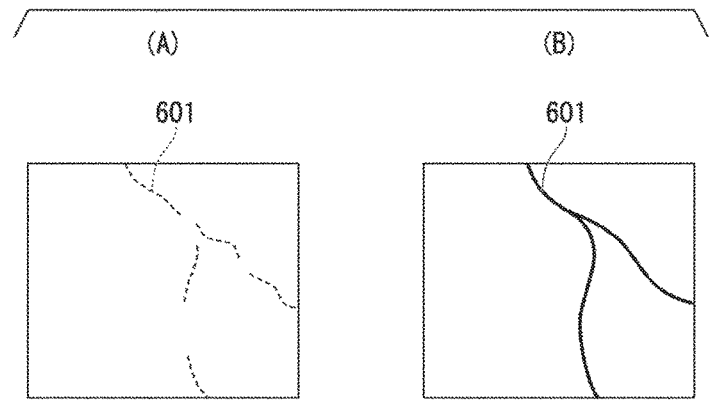
FIG. 6 is a diagram which shows image examples before and after spatial frequency resolution processing, emphasis processing, and color conversion processing are performed in the first embodiment of the present invention.

Then, image processing is performed on the generated wavelength image as shown in, for example, the following (1) to (3), and thereby a relatively thick blood vessel (for example, a blood vessel with a thickness of 1 to 2 mm) at a deep portion under a mucous membrane is image-processed as shown in FIG. 6.

(1) Spatial frequency resolution processing: processing to generate a band image on which filtering processing with different spatial frequencies is performed for each generated wavelength image.

(2) Emphasis processing: processing to multiply a pixel value of the band image generated in (1) the spatial frequency resolution processing by, for example, an emphasis coefficient held in table data.

(3) Color conversion processing: processing to improve a contrast of a thick blood vessel with respect to a background mucous membrane by using, for example, a predetermined color conversion matrix for the band image generated by (1) the spatial frequency resolution processing or images processed by (2) the emphasis processing.

FIG. 6 is a diagram which shows image examples before and after spatial frequency resolution processing, emphasis processing, and color conversion processing are performed. FIG. 6(A) shows an image example before the spatial frequency resolution processing, the emphasis processing, and the color conversion processing are performed. In the example shown, a blood vessel 601 is thinly displayed. FIG. 6(B) shows an image example after the spatial frequency resolution processing, the emphasis processing, and the color conversion processing are performed. In the example shown, the blood vessel 601 is displayed with emphasis.

Signal transmission between the first substrate 101 and the second substrate 102 may be performed in any method. For example, the signal transmission between the first substrate 101 and the second substrate 102 may be performed by providing a through electrode between the first substrate 101 and the second substrate 102. For example, the signal transmission between the first substrate 101 and the second substrate 102 may be performed by providing a transmission path outside the first substrate 101 and the second substrate 102.

Figure 7:
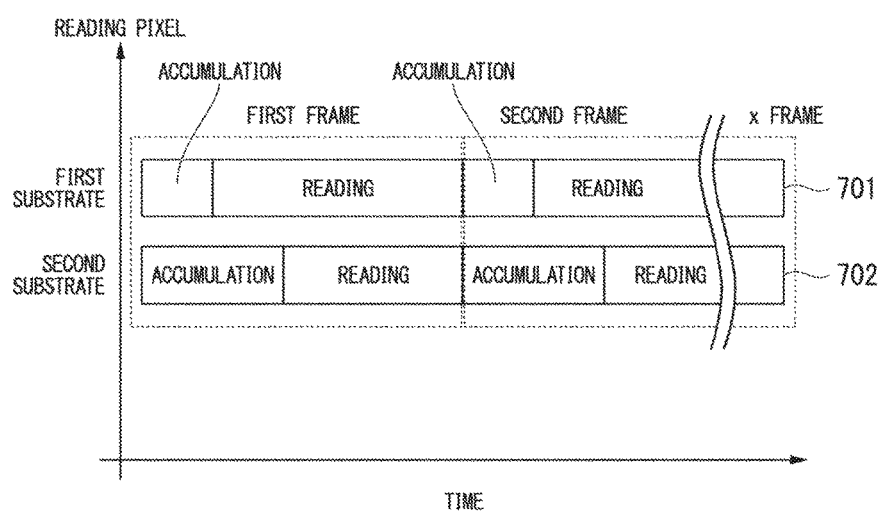
FIG. 7 is a timing chart which shows a driving timing of the imaging element according to the first embodiment of the present invention.

Next, a drive timing of the imaging element 100 will be described. FIG. 7 is a timing chart which shows a drive timing of the imaging element 100 according to the present embodiment. A timing chart 701 which shows a drive timing of the first pixel 103 included in the first substrate 101 and a timing chart 702 which shows a drive timing of the second pixel 104 included in the second substrate 102 are shown in the example shown. The horizontal axis of the timing chart represents time.

As shown in FIG. 7, a charge accumulation time (exposure time) of the second pixel 104 is longer than a charge accumulation time (exposure time) of the first pixel 103 in the present embodiment. This is because the second pixel 104 is irradiated with only light which has passed through the first substrate 101 and therefore an amount of light with which the second pixel 104 is irradiated is smaller than an amount of light with which the first pixel 103 is irradiated. In the present embodiment, a reading time which is a time to read a signal from each pixel is set such that exposure start timings of the first pixel 103 and the second pixel 104 become a start timing of the same frame.

As described above, according to the present embodiment, the first substrate 101 and the second substrate 102 are stacked. The second substrate 102 is disposed at a position overlapping the first substrate 101 and on a side opposite to a light-receiving surface side of the first substrate 101 as seen from the light-receiving surface of the first substrate 101. The first substrate 101 transmits light. Moreover, the second substrate 102 is irradiated with the light which has passed through the first substrate 101.

As a result, it is possible to expose the first pixels 103 of the first substrate 101 and the second pixels 104 of the second substrate 102 at the same time. That is, generation of the first signal (R signal) by the first pixels 103-1, the second signal (G signal) by the first pixels 103-2, the third signal (B signal) by the first pixels 103-3, and the fourth signal (R' signal) by the second pixels 104 can be performed at the same time. Accordingly, deviation in imaging timing of each wavelength can be prevented from occurring. This enables the spectroscopic signal generation unit 501 to generate images such that positional deviation of each wavelength does not occur. Therefore, for example, when an image generated by the spectroscopic signal generation unit 501 is an image that emphasizes a blood vessel, an accurate position of the blood vessel can be known.

In the present embodiment, various types of circuits are disposed as the circuit portions 105 under the first pixel 103-2 (G pixel) and the first pixel 103-3 (B pixel) which do not easily transmit the light having a peak wavelength of 630 nm (red light), and thereby it is possible increase aperture ratios of the first pixels 103-1 to 103-3 and the second pixel 104. Accordingly, S/N ratios of the first to third signals output by the first pixels 103-1 to 103-3 can be increased, and an S/N ratio of the fourth signal output by the second pixel can be increased.

In the example described above, the second pixel 104 is the R' pixel, but an IR pixel including a filter transmitting only near infrared light or a pixel without a filter (W pixel, clear pixel) may be disposed instead of the second pixel 104.

(Second Embodiment)

Next, a second embodiment of the present invention will be described. A difference between an imaging device of the present embodiment and the imaging device 1 of the first embodiment is the configuration of an imaging element. The imaging element 100 of the first embodiment is different from an imaging element 800 of the present embodiment in that a third pixel 805 is provided on a second substrate 802. An arrangement of the second pixels 104 in the second substrate 802, the circuit portions 105, and the third pixels 805 in the present embodiment is different from that in the first embodiment. The other configurations are the same as in the first embodiment.

Figure 8:
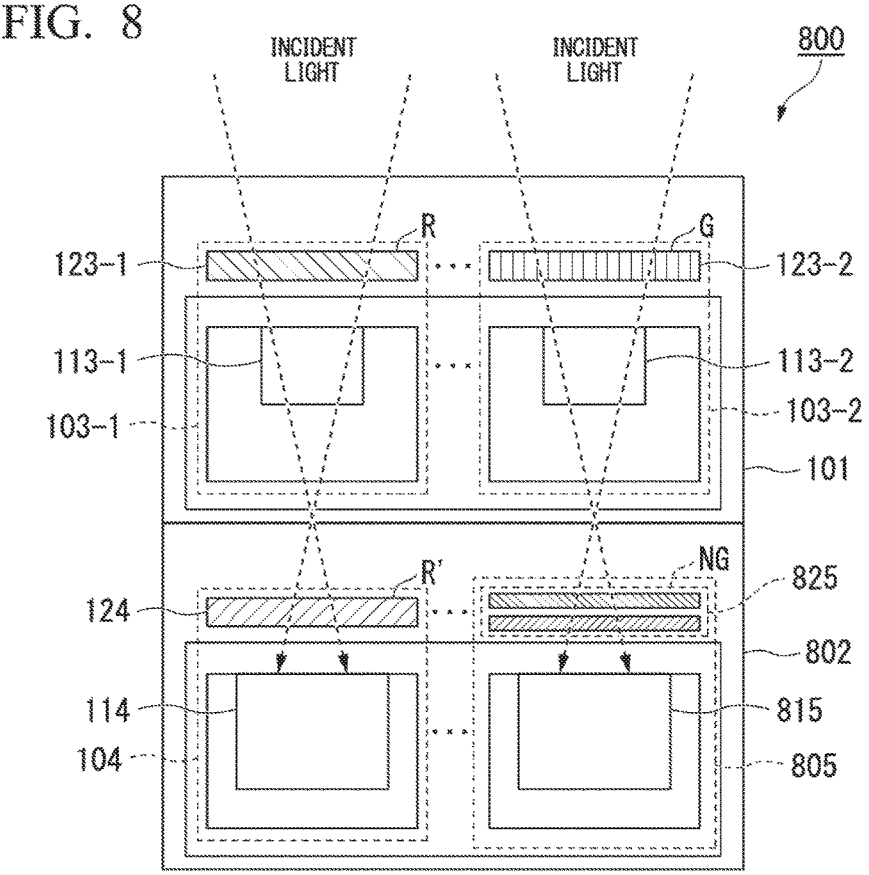
FIG. 8 is a sectional diagram which shows a cross-section of an imaging element according to a second embodiment of the present invention.

FIG. 8 is a sectional diagram which shows a cross-section of an imaging element 800 according to a second embodiment of the present invention. In the example shown, the imaging element 800 includes the first substrate 101, the second substrate 802, the plurality of first pixels 103, the plurality of second pixels 104, and a plurality of third pixels 805. Although not shown in FIG. 8, the imaging element 800 includes the plurality of circuit portions 105. A side irradiated with incident light is set as a light-receiving surface.

The first substrate 101 and the second substrate 802 are stacked. The first substrate 101 and the second substrate 802 are silicon substrates. The first substrate 101 transmits a portion of incident light.

The configurations of the first substrate 101, the first pixel 103, the second pixel 104, and the circuit portion 105 are the same as in the first embodiment. The third pixels 805 are arranged in the second substrate 801. The third pixels 805 include a third photodiode 815 for detecting light and a Fabry-Perot filter 825 for transmitting light in a narrow band having a peak wavelength of 540 nm (green light). Accordingly, the third pixels 805 output a fifth signal (an NG signal, a narrow green signal) in accordance with an exposure amount of the light in a narrow band having a peak wavelength of 540 nm (green light) among the incident light. Hereinafter, the third pixels 805 are referred to as NG pixels.

Figure 9:
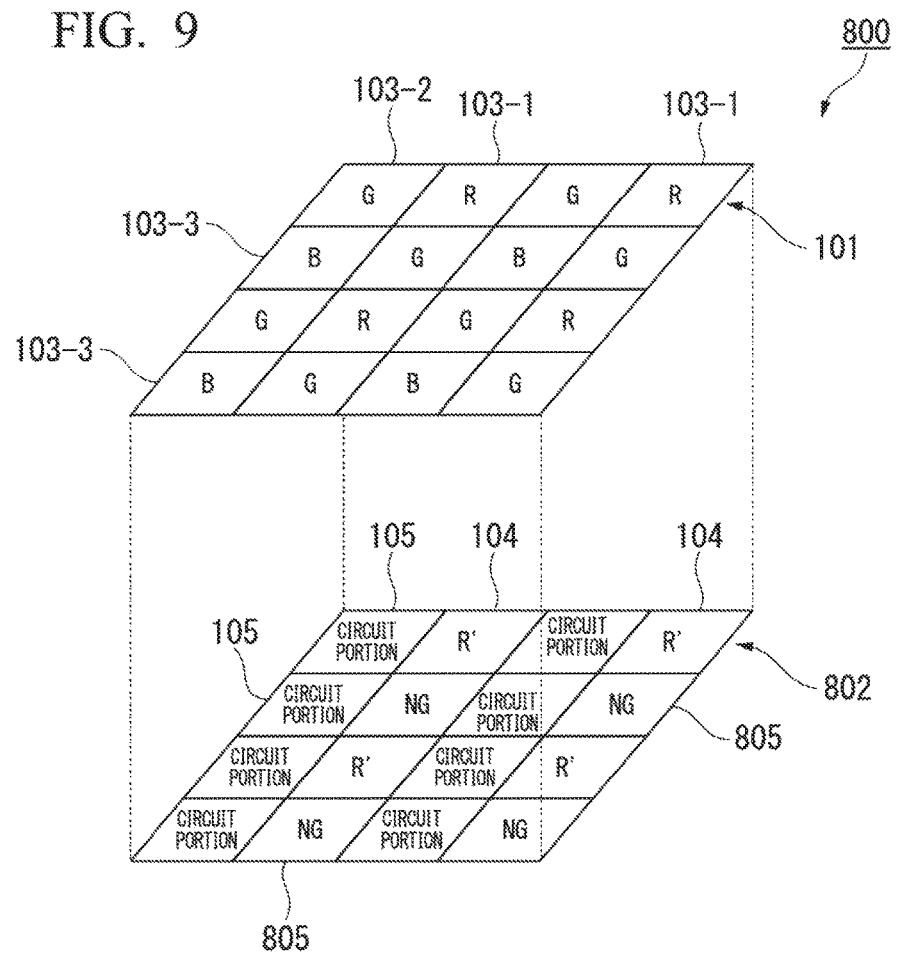
FIG. 9 is a schematic diagram which shows an arrangement of a first pixel, a second pixel, a third pixel, and a circuit portion according to the second embodiment of the present invention.

Next, an arrangement of the first pixel 103, the second pixel 104, the third pixel 805, and the circuit portion 105 will be described. FIG. 9 is a schematic diagram which shows the arrangement of the first pixel 103, the second pixel 104, the third pixel 805, and the circuit portion 105 according to the present embodiment. In the example shown in FIG. 9, sixteen first pixels 103 regularly arranged in a two-dimensional shape of four rows and four columns are included in the first substrate 101. Four second pixels 104, four third pixels 805, and eight circuit portions 105 regularly arranged in the two-dimensional shape of four rows and four columns are included in the second substrate 802.

As shown in FIG. 9, the first pixel 103-1 (R pixel), the first pixel 103-2 (G pixel), and the first pixel 103-3 (B pixel) are arranged in a Bayer arrangement in the first substrate 101. Incident light is directly incident on the first pixels 103-1 to 103-3. Therefore, it is possible to output a first signal (R signal) in accordance with an exposure amount of red light among the incident light, a second signal (G signal) in accordance with an exposure amount of green light among the incident light, and a third signal (B signal) in accordance with an exposure amount of blue light among the incident light in the first substrate 101.

The circuit portions 105 are arranged in a first column and a third column of the second substrate 802. Moreover, the second pixels 104 and the third pixels 805 are alternately arranged in a second column and a fourth column of the second substrate 802. The second pixels 104 are arranged at positions corresponding to the first pixels 103-1 (for example, positions immediately under the first pixels 103-1). The third pixels 805 are arranged at positions corresponding to the first pixels 103-2 (for example, positions immediately under the first pixels 103-2).

With such an arrangement, light which has passed through the first pixel 103-1 of the first substrate 101 among the incident light is incident on the second pixel 104. The color filter 123-1 included in the first pixel 103-1 transmits the light having a peak wavelength of 600 nm (red light). Moreover, the first substrate 101 is a silicon substrate and transmits light in a wavelength band including a wavelength of red light. Therefore, the light having a peak wavelength of 600 nm (red light) among the incident light is incident on the second pixel 104 of the second substrate 102.

Accordingly, even if the first pixel 103-1 of the first substrate 101 is present on a light-receiving surface side of the second pixel 104 of the second substrate 102, the second pixel 104 can output a fourth signal (an R' signal, a red' signal) in accordance with an exposure amount of the light having a peak wavelength of 630 nm (red light) among the incident light.

With such an arrangement, light which has passed through the first pixel 103-2 of the first substrate 101 among the incident light is incident on the third pixel 805. The color filter 123-2 included in the first pixel 103-2 transmits the light having a peak wavelength of 540 nm (green light). Moreover, the first substrate 101 is a silicon substrate and transmits light in a wavelength band including a wavelength of green light. Therefore, the light having a peak wavelength of 540 nm (green light) among the incident light is incident on the third pixel 805 of the second substrate 102.

Accordingly, even if the first pixel 103-2 of the first substrate 101 is present on a light-receiving surface side of the third pixel 805 of the second substrate 102, the third pixel 805 can output a fifth signal (an NG signal, a narrow green signal) in accordance with an exposure amount of the light having a peak wavelength of 540 nm (green light) among the incident light.

The number and arrangement of the first pixels 103-1 to 103-3 included in the first substrate 101, the second pixels 104 included in the second substrate 802, the third pixels 805, and the circuit portions 105 are not limited to the example shown in FIG. 9, and may be any number and arrangement. The second pixel 104 is disposed under the first pixel 103-1 in a corresponding manner, but the present invention is not limited thereto. For example, it is possible to devise such a method that a pixel size of the second pixel 104 is set to a size different from a pixel size of the first pixel 103-1 (for example, an integral multiple of the first pixel 103-1). In the example shown in FIG. 9, the third pixels 805 are arranged under some of the first pixels 103-2 in a corresponding manner, but the present embodiment is not limited thereto. For example, it is possible to devise such a method that a pixel size of the third pixel 805 is set to a size different from a pixel size of the first pixel 103-2 (for example, an integral multiple of the first pixel 103-2). Moreover, it is possible to devise such a method that a size of the circuit portion 105 is set to a size different from the pixel size of the first pixel 103-2 or the first pixel 103-3.

Since the first pixels 103-1 to 103-3, the second pixels 104, and the third pixels 805 are irradiated with incident light at the same time due to the arrangement of the first pixels 103-1 to 103-3, the second pixels 104, the third pixels

805 described above, it is possible to simultaneously output the first signal (R signal), the second signal (G signal), the third signal (B signal), the fourth signal (R' signal), and the fifth signal (NG signal) at the same time. As a result, positional deviation can be prevented from occurring in images of each wavelength.

Figure 10:
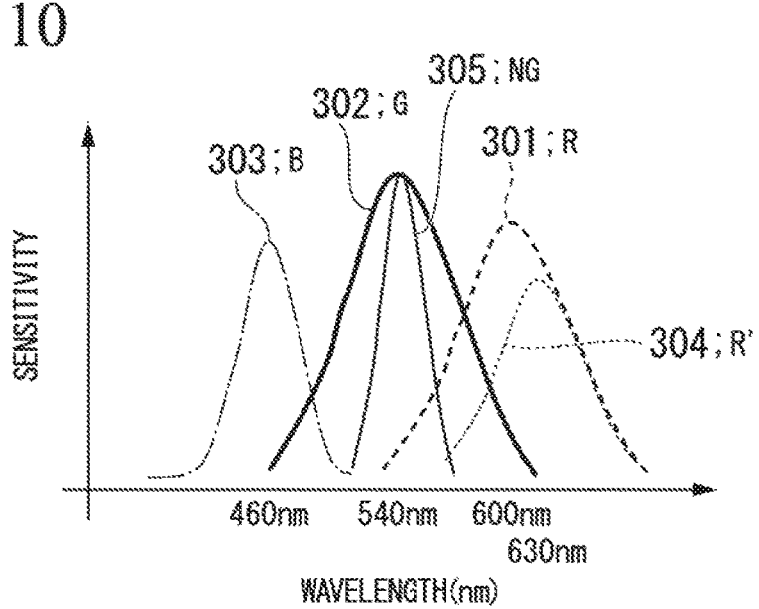
FIG. 10 is a graph which shows sensitivity of the first pixel, the second pixel, and the third pixel according to the second embodiment of the present invention.

FIG. 10 is a graph which shows sensitivity of the first pixels 103-1 to 103-3, the second pixel 104, and the third pixel 805 in the present embodiment. The horizontal axis of the graph represents a wavelength (nm). The vertical axis of the graph represents the sensitivity of the first pixels 103-1 to 103-3, the second pixel 104, and the third pixel 805.

The line 301 is a line indicating the sensitivity of the first pixel 103-1 (R pixel). As shown in FIG. 10, the first pixel 103-1 (R pixel) has sensitivity in accordance with the wavelength band having a peak wavelength of 600 nm. The line 302 is a line indicating the sensitivity of the first pixel 103-2 (G pixel). As shown in FIG. 10, the first pixel 103-2 (G pixel) has sensitivity in accordance with the wavelength band having a peak wavelength of 540 nm.

The line 303 is a line indicating the sensitivity of the first pixel 103-3 (B pixel). As shown in FIG. 10, the first pixel 103-3 (B pixel) has the sensitivity in accordance with the wavelength band having a peak wavelength of 460 nm. The line 304 is a line indicating the sensitivity of the second pixel 104 (R' pixel). As shown in FIG. 10, the second pixel 104 (R' pixel) has the sensitivity in accordance with the wavelength band having a peak wavelength of 630 nm. A line 305 is a line indicating the sensitivity of the third pixel 805 (NG pixel). As shown in FIG. 10, the third pixel 805 (NG pixel) has the sensitivity to a band which is the wavelength band having a peak wavelength of 540 nm and is narrower than that of the first pixel 103-2 (G pixel).

A configuration and an operation of an imaging device including the imaging element 800 are the same as those of the imaging device 1 in the first embodiment. For example, an image processing method by the spectroscopic signal generation unit 501 is the same method as in the first embodiment. Since the fifth signal (NG signal) output by the third pixel 805 can be obtained in the present embodiment, it is possible to improve an image quality by using the fifth signal (NG signal) for image processing.

As described above, according to the present embodiment, the first substrate 101 and the second substrate 802 are stacked. The second substrate 802 is disposed at a position overlapping the first substrate 101 and on a side opposite to a light-receiving surface side of the first substrate 101 as seen from the light-receiving surface of the first substrate 101. The first substrate 101 transmits light. Moreover, the second substrate 802 is irradiated with the light which has passed through the first substrate 101.

As a result, it is possible to expose the first pixels 103 of the first substrate 101, the second pixels 104 of the second substrate 802, and the third pixels 805 of the second substrate 802 at the same time. That is, generation of the first signal (R signal) by the first pixels 103-1, the second signal (G signal) by the first pixels 103-2, the third signal (B signal) by the first pixels 103-3, the fourth signal (R' signal) by the second pixels 104, and the fifth signal (NG signal) by the third pixels 805 can be performed at the same time. Accordingly, deviation in imaging timing of each wavelength can be prevented from occurring. This enables the spectroscopic signal generation unit 501 to generate images such that positional deviation of each wavelength does not occur. For example, when an image generated by the spectroscopic signal generation unit 501 is an image that emphasizes a blood vessel, an accurate position of the blood vessel can be known.

In the present embodiment, description is provided using an example in which the third pixel 805 includes the Fabry-Perot filter 825, but the present embodiment is not limited thereto. For example, any filter that can realize characteristics of a narrow band wavelength may be used in the third pixel 805 instead of the Fabry-Perot filter 825.

(Third Embodiment)

Next, a third embodiment of the present invention will be described. A difference between an imaging device of the present embodiment and the imaging device 1 of the first embodiment is the configuration of the imaging element. The imaging element 100 of the first embodiment and an imaging element 1100 of the present embodiment have different types of light detected by first pixels 1003 included in a first substrate 1001. An arrangement of the first pixels 1003 in the first substrate 1001 and an arrangement of second pixels 104 and circuit portions 105 in a second substrate 1002 are different between these imaging elements. The other configurations are the same as in the first embodiment.

The imaging element 1100 includes the first substrate 1001, the second substrate 1002, a plurality of first pixels 1003, the plurality of second pixels 104, and the plurality of circuit portions 105. A side irradiated with incident light is set to a light-receiving surface.

The first substrate 1001 and the second substrate 1002 are stacked. The first substrate 1001 and the second substrate 1002 are silicon substrates. The first substrate 1001 transmits a portion of incident light.

The first pixels 1003 are arranged in the first substrate 1001. Among the first pixels 1003, a first pixel 1003-1 includes a first photodiode 1013-1 for detecting light, and a color filter 1023-1 for transmitting cyan light. As a result, the first pixel 1003-1 outputs a sixth signal (Cy signal, a cyan signal) in accordance with an exposure amount of cyan light among the incident light. Hereinafter, the first pixel 1003-1 is referred to as a Cy pixel.

Among the first pixels 1003, a first pixel 1003-2 includes a first photodiode 1013-2 for detecting light and a color filter 1023-2 for transmitting yellow light. As a result, the first pixel 1003-2 outputs a seventh signal (Ye signal, a yellow signal) in accordance with an exposure amount of yellow light among the incident light. Hereinafter, the first pixel 1003-2 is referred to as a Ye pixel.

Among the first pixels 1003, a first pixel 1003-3 includes a first photodiode 1013-3 for detecting light and a color filter 1023-3 for transmitting magenta light. As a result, the first pixel 1003-3 outputs an eighth signal (Mg signal, a magenta signal) in accordance with an exposure amount of magenta light among the incident light. Hereinafter, the first pixel 1003-3 is referred to as an Mg pixel.

Among the first pixels 1003, a first pixel 1003-4 includes a first photodiode 1013-4 for detecting light and a color filter 1023-4 for transmitting green light. As a result, the first pixel 1003-4 outputs a ninth signal (G signal, a green signal) in accordance with an exposure amount of green light among the incident light. Hereinafter, the first pixel 1003-4 is referred to as a G pixel.

The second pixels 104 and the circuit portions 105 are arranged in the second substrate 1002. The configuration of the second pixels 104 and the circuit portions 105 is the same as in the first embodiment. The circuit portions 105 include various types of circuits.

Figure 11:
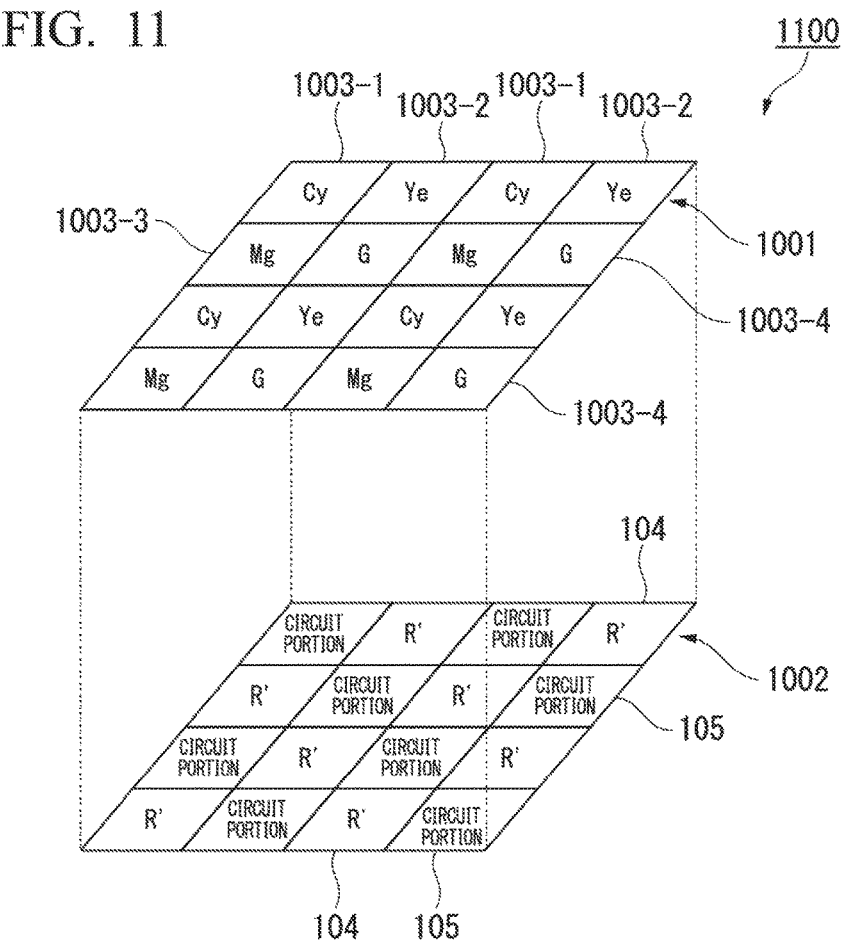
FIG. 11 is a schematic diagram which shows an arrangement, of a first pixel, a second pixel, and a circuit portion according to a third embodiment of the present invention.

Next, the arrangement of the first pixels 1003, the second pixels 104, and the circuit portions 105 will be described. FIG. 11 is a schematic diagram which shows the arrangement of the first pixels 1003, the second pixels 104, and the circuit portions 105 in the present embodiment. In an example shown in FIG. 11, sixteen first pixels 1003 regularly arranged in a two-dimensional shape of four rows and four columns are included in the first substrate 1001. Eight second pixels 104 and eight circuit portions 105 regularly arranged in the two-dimensional shape of four rows and four columns are included in the second substrate 1002.

As shown in FIG. 11, the first pixels 1003-1 (Cy pixels) and the first pixels 1003-3 (Mg pixels) are alternately arranged in the first and third columns (odd-numbered columns) of the first substrate 1001. The first pixels 1003-2 (Ye pixels) and the first pixels 1003-4 (G pixels) are alternately arranged in the second and fourth columns (even-numbered columns) of the first substrate 1001.

Incident light is directly incident on the first pixels 1003-1 to 1003-4. As a result, it is possible to output the sixth signal (Cy signal) in accordance with an exposure amount of cyan light among the incident light, the seventh signal (Ye signal) in accordance with an exposure amount of yellow light among the incident light, the eighth signal (Mg signal) in accordance with an exposure amount of magenta light among the incident light, and the ninth signal (G signal) in accordance with an exposure amount of green light among the incident light in the first substrate 1001.

As shown in FIG. 11, the second pixels 104 are arranged at positions corresponding to the first pixels 1003-2 and the first pixels 1003-3 (for example, positions immediately under the first, pixels 1003-2 and positions immediately under the first pixels 1003-3) in the second substrate 1002. Moreover, the circuit portions 105 are arranged at positions corresponding to the first pixels 1003-1 and the first pixels 1003-4 (for example, positions immediately under the first pixels 1003-1 and positions immediately under the first pixels 1003-4) in the second substrate 1002.

With such an arrangement, light which has passed through the first pixel 1003-2 of the first substrate 1001 among the incident light or light which has passed through the first pixel 1003-3 of the first substrate 1001 among the incident light is incident on the second pixel 104. The color filter 1023-2 included in the first pixel 1003-2 transmits yellow light. Moreover, the color filter 1023-3 included in the first pixel 1003-3 transmits magenta light. Moreover, the first substrate 1001 is a silicon substrate and transmits light in a wavelength band of 500 nm to 1100 nm. Therefore, at least the light having a peak wavelength of 600 nm (red light) among the incident light is incident on the second pixel 104 of the second substrate 1002.

Therefore, even if the first pixel 1003-2 or the first pixel 1003-3 of the first substrate 1001 is present on the light-receiving surface side of the second pixel 104 of the second substrate 1002, the second pixel 104 can output the fourth signal (R' signal, a red' signal) in accordance with an exposure amount of the light having a peak wavelength of 630 nm (red light) among the incident light.

The color filter 1023-1 included in the first pixel 1003-1 transmits only cyan light. That is, the color filter 1023-1 does not transmit red light. The color filter 1023-4 included in the first pixel 1003-4 transmits only green light. That is, the color filter 1023-4 does not transmit red light. Therefore, light passing through the first pixel 1003-1 and the first pixel 1003-4 does not include red light.

Accordingly, even if the second pixels 104 are arranged under the first pixel 1003-1 and the first pixel 1003-4, it is difficult to accurately detect the light having a peak wavelength of 630 nm (red light). For example, if various types of circuits are arranged around the first pixels 103 and the second pixels 104, it is considered that the aperture ratios of the first pixels 103 and the second pixels 104 decrease and the S/N ratios of the first to fourth signals decrease.

In the present embodiment, various types of circuits are arranged as the circuit portions 105 under the first pixel 1003-1 (Cy pixel) and the first pixel 1003-4 (G pixel) which are difficult to transmit the light having a peak wavelength of 630 nm (red light), and thereby the aperture ratios of the first pixels 1003-1 to 1003-4 and the second pixel 104 can increase. Accordingly, it is possible to increase the S/N ratios of the sixth to ninth signals output by the first pixels 1003-1 to 1003-4. Moreover, it is possible to increase the S/N ratio of the fourth signal output by the second pixel 104.

The number and arrangement of the first pixels 1003-1 to 1003-4 included in the first substrate 1001 and the second pixels 104 and the circuit portions 105 included in the second substrate 1002 are not limited to the example shown in FIG. 11, and may be any number and arrangement. In the example shown in FIG. 11, the second pixels 104 are arranged under the first pixels 1003-2 and the first pixels 1003-3 in a corresponding manner, but the present embodiment is not limited thereto. For example, it is possible to devise such a method that a pixel size of the second pixel 104 is set to a size different from a pixel size of the first pixel 1003-2 or the first pixel 1003-3 (for example, an integral multiple of the first pixel 1003-2 or the first pixel 1003-3). For example, it is possible to devise such a method that a size of the circuit portion 105 is set to a size different from a pixel size of the first pixel 1003-1 or the first pixel 1003-4.

Since the first pixels 1003-1 to 1003-4 and the second pixels 104 are irradiated with incident light at the same time due to the arrangement of the first pixels 1003-1 to 1003-4 and the second pixels 104 described above, it is possible to simultaneously output the sixth signal (Cy signal), the seventh signal (Ye signal), the eighth signal (Mg signal), the ninth signal (G signal), and the fourth signal (R' signal) at the same time. As a result, a positional deviation can be prevented from occurring in images of each wavelength.

Figure 12:
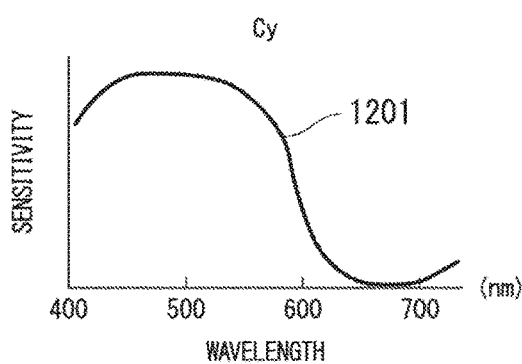
FIG. 12 is a graph which shows sensitivity of the first pixel in the third embodiment of the present invention.

FIG. 12 is a graph which shows sensitivity of the first pixel 1003-1 in the present embodiment. The horizontal axis of the graph represents a wavelength (nm), and the vertical axis of the graph represents sensitivity of the first pixel 1003-1.

A line 1201 is a line indicating the sensitivity of the first pixel 1003-1 (Cy pixel). As shown in FIG. 12, the first pixel 1003-1 (Cy pixel) does not have sensitivity to the light having a peak wavelength of 630 nm (red light). That is, the first pixel 1003-1 (Cy pixel) does not transmit the light having a peak wavelength of 630 nm (red light).

Figure 13:
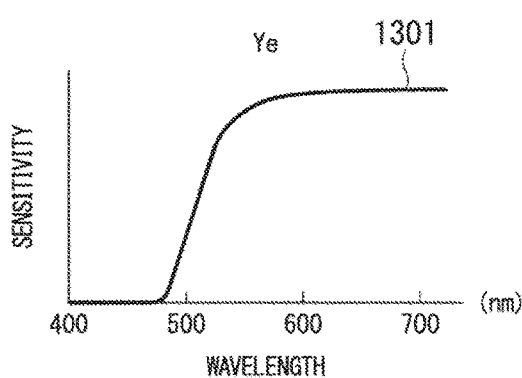
FIG. 13 is a graph which shows the sensitivity of the first pixel in the third embodiment of the present invention.

FIG. 13 is a graph which shows the sensitivity of the first pixel 1003-2 in the present embodiment. The horizontal axis of the graph represents a wavelength (nm), and the vertical axis of the graph represents sensitivity of the first pixel 1003-2.

A line 1301 is a line indicating the sensitivity of the first pixel 1003-2 (Ye pixel.). As shown in FIG. 13, the first pixel 1003-2 (Ye pixel) has sensitivity to the light having a peak wavelength of 630 nm (red light). That is, the first pixel 1003-2 (Ye pixel) transmits the light having a peak wavelength of 630 nm (red light).

Figure 14:
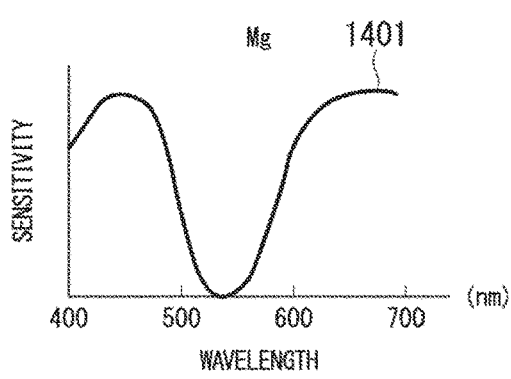
FIG. 14 is a graph which shows the sensitivity of the first pixel in the third embodiment of the present invention.

FIG. 14 is a graph which shows the sensitivity of the first pixel 1003-3 in the present embodiment. The horizontal axis of the graph represents a wavelength (nm), and the vertical axis of the graph represents the sensitivity of the first pixel 1003-3.

A line 1401 is a line indicating the sensitivity of the first pixel 1003-3 (Mg pixel). As shown in FIG. 14, the first pixel 1003-3 (Mg pixel) has sensitivity to the light having a peak wavelength of 630 nm (red light). That is, the first pixel 1003-3 (Mg pixel) transmits the light having a peak wavelength of 630 nm (red light).

The configuration and operation of an imaging device including the imaging element 1100 are the same as those of the imaging device 1 in the first embodiment. For example, an image processing method by the spectroscopic signal generation unit 501 is the same method as that in the first embodiment. The Cy signal, the Ye signal, and the Mg signal, instead of the R signal and B signal, can be obtained in the present embodiment. Since R=Ye−G and B=Cy−G according to relationships such as Ye=R+G, Cy=G+B, and Mg=R+B, it is possible to generate these signals by calculating the R signal and the B signal.

As described above, according to the present embodiment, the first substrate 1001 and the second substrate 1002 are stacked. The second substrate 1002 is disposed at a position overlapping the first substrate 1001 and on a side opposite to a light-receiving surface side of the first substrate 1001 as seen from the light-receiving surface of the first substrate 1001. The first substrate 1001 transmits light. Moreover, the second substrate 1002 is irradiated with the light which has passed through the first substrate 1001.

As a result, it is possible to expose the first pixels 1003 of the first substrate 1001 and the second pixels 104 of the second substrate 1002 at the same time. That is, generations of the sixth signal (Cy signal) by the first pixels 1003-1, the seventh signal (Ye signal) by the first pixels 1003-2, the eighth signal (Mg signal) by the first pixels 1003-3, the ninth signal (G signal) by the first pixels 1003-4, and the fourth signal (R' signal) by the second pixels 104 can be performed at the same time. Accordingly, a deviation in imaging timing of each wavelength can be prevented from occurring. This enables the spectroscopic signal generation unit 501 to generate images such that a positional deviation of each wavelength does not occur. Therefore, for example, when an image generated by the spectroscopic signal generation unit 501 is an image that emphasizes a blood vessel, an accurate position of the blood vessel can be known.

(Fourth Embodiment)

Next, a fourth embodiment of the present invention will be described. A difference between an imaging device of the present embodiment and the imaging device 1 of the first embodiment is the configuration of an imaging element. The imaging element 100 of the first embodiment and an imaging element 1500 of the present embodiment have different types of light detected by first pixels 1503 included in a first substrate 1501. An arrangement of the first pixels 1503 in the first substrate 1501 and an arrangement of second pixels 104 and circuit portions 105 in a second substrate 1502 are different between these imaging elements. The other configurations are the same as in the first embodiment.

The imaging element 1500 includes the first substrate 1501, the second substrate 1502, a plurality of first pixels 1503, the plurality of second pixels 104, and the plurality of circuit portions 105. A side irradiated with incident light is set to a light-receiving surface.

The first substrate 1501 and the second substrate 1502 are stacked. The first substrate 1501 and the second substrate 1502 are silicon substrates. The first substrate 1501 transmits a portion of incident light.

The first pixels 1503 are arranged in the first substrate 1501. Among the first pixels 1503, a first pixel 1503-1 includes a first photodiode 1513-1 for detecting light, and a color filter 1523-1 for transmitting the light having a peak wavelength of 600 nm (red light). As a result, the first pixel 1503-1 outputs a first signal (R signal, a red signal) in accordance with an exposure amount of the light having a peak wavelength of 600 nm (red light) among the incident light. Hereinafter, the first pixel 1503-1 is referred to as an R pixel Among the first pixels 1503, a first pixel 1503-2 includes a first photodiode 1513-2 for detecting light. The first pixel 1503-2 does not include a color filter. As a result, the first pixel 1503-2 outputs a tenth signal (W signal, a clear signal) in accordance with an exposure amount of the incident light. Hereinafter, the first pixel 1503-2 is referred to as a W pixel (clear pixel).

Among the first pixels 1503, a first pixel 1503-3 includes a first photodiode 1513-3 for detecting light and a color filter 1523-3 for transmitting the light having a peak wavelength of 460 nm (blue light). As a result, the first pixel 1503-3 outputs the third signal (B signal, a blue signal) in accordance with an exposure amount of the light having a peak wavelength of 460 nm (blue light) among the incident light. Hereinafter, the first pixel 1503-3 is referred to as a B pixel.

The second pixels 104 and the circuit portions 105 are arranged in the second substrate 1502. The configurations of the second pixels 104 and the circuit portions 105 are the same as in the first embodiment. The circuit portions 105 include various types of circuits.

Figure 15:
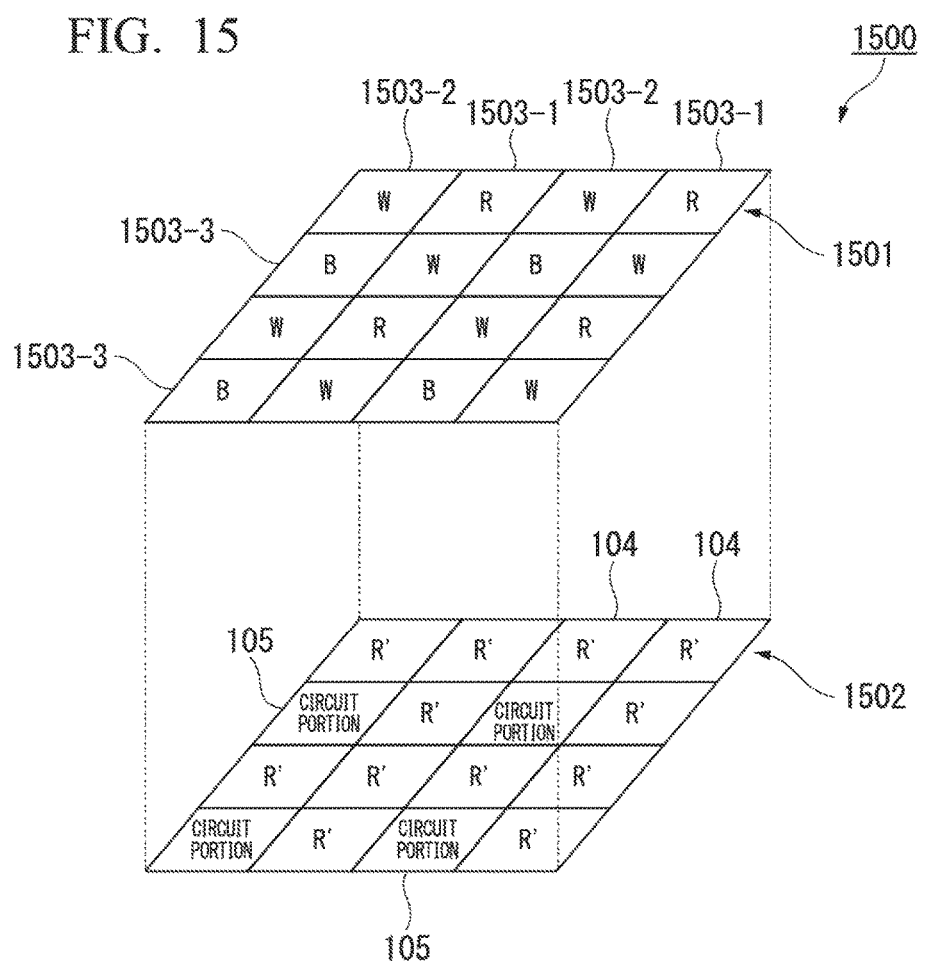
FIG. 15 is a schematic diagram which shows an arrangement of a first pixel, a second pixel, and a circuit portion according to a fourth embodiment of the present invention.

Next, the arrangement of the first pixels 1503, the second pixels 104, and the circuit portions 105 will be described. FIG. 15 is a schematic diagram which shows the arrangement of the first pixels 1503, the second pixels 104, and the circuit portions 105 in the present embodiment. In an example shown in FIG. 15, sixteen first pixels 1503 regularly arranged in a two-dimensional shape of four rows and four columns are included in the first substrate 1501. Eight second pixels 104 and eight circuit portions 105 regularly arranged in the two-dimensional shape of four rows and four columns are included in the second substrate 1502.

As shown in FIG. 15, the first pixels 1503-2 (W pixels), instead of G pixels in the Bayer arrangement, are arranged in the first substrate 1501. The arrangement of the first pixels 1503-1 (R pixels) and the first pixels 1503-3 (B pixels) is the same as the Bayer arrangement.

Incident light is directly incident on the first pixels 1503-1 to 1503-3. Therefore, it is possible to output the first signal (R signal) in accordance with an exposure amount of red light among the incident light, the tenth signal (W signal) in accordance with an exposure amount of the incident light, and the third signal (B signal) in accordance with an exposure amount of blue light among the incident light in the first substrate 1501.

As shown in FIG. 15, the second pixels 104 are arranged at positions corresponding to the first pixels 1503-1 and the first pixels 1503-2 (for example, positions immediately under the first pixels 1503-1 and positions immediately under the first pixels 1503-2) in the second substrate 1502. Moreover, the circuit portions 105 are arranged at positions corresponding to the first pixels 1503-3 (for example, positions immediately under the first pixels 1503-3) in the second substrate 102.

With such an arrangement, light which has passed through the first pixels 1503-1 or the first pixels 1503-2 of the first substrate 1501 among the incident light is incident on the second pixels 104. The color filters 1523-1 included in the first pixels 1503-1 transmit the light having a peak wavelength of 600 nm (red light). Moreover, the first pixels 1503-2 do not include color filters. Moreover, the first substrate 1501 is a silicon substrate and transmits light in a wavelength band including the wavelength of red light. Therefore, light including the light having a peak wavelength of 630 nm (red light) is incident on the second pixels 104 of the second substrate 1502.

Therefore, even if the first pixels 1503-1 or the first pixels 1503-2 of the first substrate 1501 are present on the light-receiving surface sides of the second pixels 104 of the second substrate 1502, the second pixels 104 can output the fourth signal (R' signal, a red' signal) in accordance with an exposure amount of the light having a peak wavelength of 630 nm (red light) among the incident light.

The color filters 1523-3 included in the first pixels 1503-3 transmit only the light having a peak wavelength of 460 nm (blue light). That is, the color filter 1523-3 does not transmit red light. Therefore, the light which has passed through the first pixels 1503-3 does not include red light.

Accordingly, even if the second pixels 104 are arranged under the first pixels 1503-3, it is difficult to accurately detect the light having a peak wavelength of 630 nm (red light). For example, if various types of circuits are arranged around the first pixels 1503 and the second pixels 104, it is considered that the aperture ratios of the first pixels 1503 and the second pixels 104 decrease and S/N ratios of the first, third, fourth, and tenth signals decrease.

In the present embodiment, various types of circuits are arranged as the circuit portions 105 under the first pixels 1503-3 (B pixel) which are difficult to transmit the light having a peak wavelength of 630 nm (red light), and thereby the aperture ratios of the first pixels 1503-1 to 1503-3 and the second pixels 104 can increase. Accordingly, it is possible to increase the S/N ratios of the first, third, and tenth signals output by the first pixels 1503-1 to 1503-3. Moreover, it is possible to increase the S/N ratio of the fourth signal output by the second pixels 104.

The number and arrangement of the first pixels 1503-1 to 1503-3 included in the first substrate 1501, and the second pixels 104 and the circuit portions 105 included in the second substrate 1502 are not limited to the example shown in FIG. 15, and may be any number and arrangement. In the example shown in FIG. 15, the second pixels 104 are arranged under the first pixels 1503-1 and the first pixels 1503-2 in a corresponding manner, but the present embodiment is not limited thereto. For example, it is possible to devise such a method that a pixel size of the second pixel 104 is set to a size different from a pixel size of the first pixel 1503-1 or the first pixel 1503-2 (for example, an integral multiple of the first pixel 1503-1 or the first pixel 1503-2). For example, it is possible to devise such a method that the size of the circuit portion 105 is set to a size different from the pixel size of the first pixel 1503-3.

Since the first pixels 1503-1 to 1503-3 and the second pixels 104 are irradiated with incident light at the same time due to the arrangement of the first pixels 1503-1 to 1503-3 and the second pixels 104 described above, it is possible to simultaneously output the first signal (R signal), the third signal (B signal), the fourth signal (R' signal), and the tenth signal (W signal) at the same time. As a result, a positional deviation can be prevented from occurring in images of each wavelength.

Figure 16:
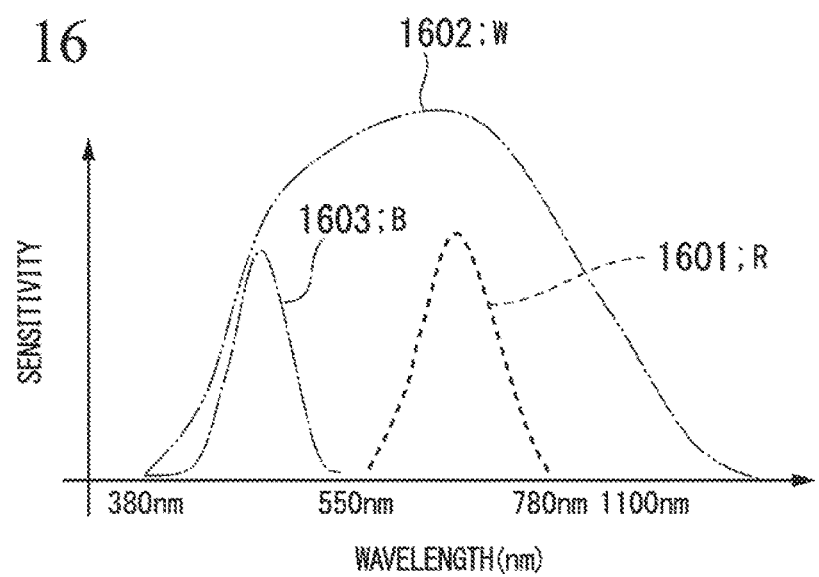
FIG. 16 is a graph which shows sensitivity of the first pixel in the fourth embodiment of the present invention.

FIG. 16 is a graph which shows sensitivity of the first pixels 1503-1 to 1503-3 in the present embodiment. The horizontal axis of the graph represents a wavelength (nm). The vertical axis of the graph represents sensitivity ox the first pixels 1503-1 to 1503-3.

A line 1601 is a line indicating the sensitivity of the first pixel 1503-1 (R pixel). As shown in FIG. 16, the first pixel 1503-1 (R pixel) has sensitivity in accordance with the wavelength band having a peak wavelength of 600 nm. A line 1602 is a line indicating the sensitivity of the first pixel 1503-2 (W pixel). As shown in FIG. 16, the first pixel 1503-2 (W pixel) has sensitivity in accordance with a wavelength band from 380 nm to 1100 nm.

A line 1603 is a line indicating the sensitivity of the first pixel 1503-3 (B pixel). As shown in FIG. 16, the first pixel 1503-3 (B pixel) has sensitivity in accordance with the wavelength band having a peak wavelength of 460 nm.

The configuration and the operation of an imaging device including the imaging element 1500 are the same as those of the imaging device 1 in the first embodiment. For example, an image processing method by the spectroscopic signal generation unit 501 is the same method as in the first embodiment. In the present embodiment, the W signal can be obtained instead of the G signal. Since G=W−(B+R), it is possible to generate the W signal by calculating the G signal.

As described above, according to the present embodiment, the first substrate 1501 and the second substrate 1502 are stacked. The second substrate 1502 is disposed at a position overlapping the first substrate 1501 and on a side opposite to a light-receiving surface side of the first substrate 1501 as seen from the light-receiving surface of the first substrate 1501. The first substrate 1501 transmits light. Moreover, the second substrate 1502 is irradiated with the light which has passed through the first substrate 1501.

As a result, it is possible to expose the first pixels 1503 of the first substrate 1501 and the second pixels 104 of the second substrate 1502 at the same time. That is, generations of the first signal (R signal) by the first pixels 1503-1, the tenth signal (W signal) by the first pixels 1503-2, the third signal (B signal) by the first pixels 1503-3, and the fourth signal (R' signal) by the second pixels 104 can be performed at the same time. Accordingly, a deviation in imaging timing of each wavelength can be prevented from occurring. This enables the spectroscopic signal generation unit 501 to generate images such that a positional deviation of each wavelength does not occur. Therefore, for example, when an image generated by the spectroscopic signal generation unit 501 is an image that emphasizes a blood vessel, an accurate position of the blood vessel can be known.

(Fifth Embodiment)

Next, a fifth embodiment of the present invention will be described. A difference between an imaging device of the present embodiment and the imaging device 1 of the first embodiment is the configuration of the imaging element. The imaging element 100 of the first embodiment and an imaging element 1700 of the present embodiment have different types of light detected by first pixels 1703 included in a first substrate 1701. An arrangement of the first pixels 1703 in the first substrate 1701 is different from in the first embodiment. The other configurations are the same as in the first embodiment.

The imaging element 1700 includes the first substrate 1701, the second substrate 102, a plurality of first pixels 1703, the plurality of second pixels 104, and the plurality of circuit portions 105. A side irradiated with incident light is set to a light-receiving surface.

The first substrate 1701 and the second substrate 102 are stacked. The first substrate 1701 and the second substrate 102 are silicon substrates. The first substrate 1701 transmits a portion of incident light.

The first pixels 1703 are arranged in the first substrate 1701. Among the first pixels 1703, a first pixel 1703-1 includes a first photodiode 1713-1 for detecting light, and a color filter 1723-1 for transmitting the light having a peak wavelength of 600 nm (red light). As a result, the first pixel 1703-1 outputs the first signal (R signal, a red signal) in accordance with an exposure amount of the light having a peak wavelength of 600 nm (red light) among the incident light. Hereinafter, the first pixel 1703-1 is referred to as an R pixel.

Among the first pixels 1703, a first pixel 1703-2 includes a first photodiode 1713-2 for detecting light and a color filter 1723-2 for transmitting the light having a peak wavelength of 540 nm (green light). As a result, the first pixel 1703-2 outputs the second signal (G signal, a green signal) in accordance with an exposure amount of the light having a peak wavelength of 540 nm (green light) among the incident light. Hereinafter, the first pixel 1703-2 is referred to as a G pixel.

Among the first pixels 1703, a first pixel 1703-3 includes a first photodiode 1713-3 for detecting light and a color filter 1723-3 for transmitting the light having a peak wavelength of 460 nm (blue light). As a result, the first pixel 1703-3 outputs the third signal (B signal, a blue signal) in accordance with an exposure amount of the light having a peak wavelength of 460 nm (blue light) among the incident light. Hereinafter, the first pixel 1703-3 is referred to as a B pixel.

Among the first pixels 1703, a first pixel 1703-4 includes a first photodiode 1713-4 for detecting light and the Fabry-Perot filter 825 for transmitting the light in a narrow band having a peak wavelength of 540 nm (green light). As a result, the first pixel 1703-4 outputs the fifth signal (NG signal, a narrow green signal) in accordance with an exposure amount of the light in a narrow band having a peak wavelength of 540 nm (green light) among the incident light. Hereinafter, the first pixel 1703-4 is referred to as an NG pixel.

The second pixels 104 and the circuit portions 105 are arranged in the second substrate 102. The configurations of the second pixels 104 and the circuit portions 105 are the same as in the first embodiment. The circuit portions 105 include various types of circuits.

Figure 17:
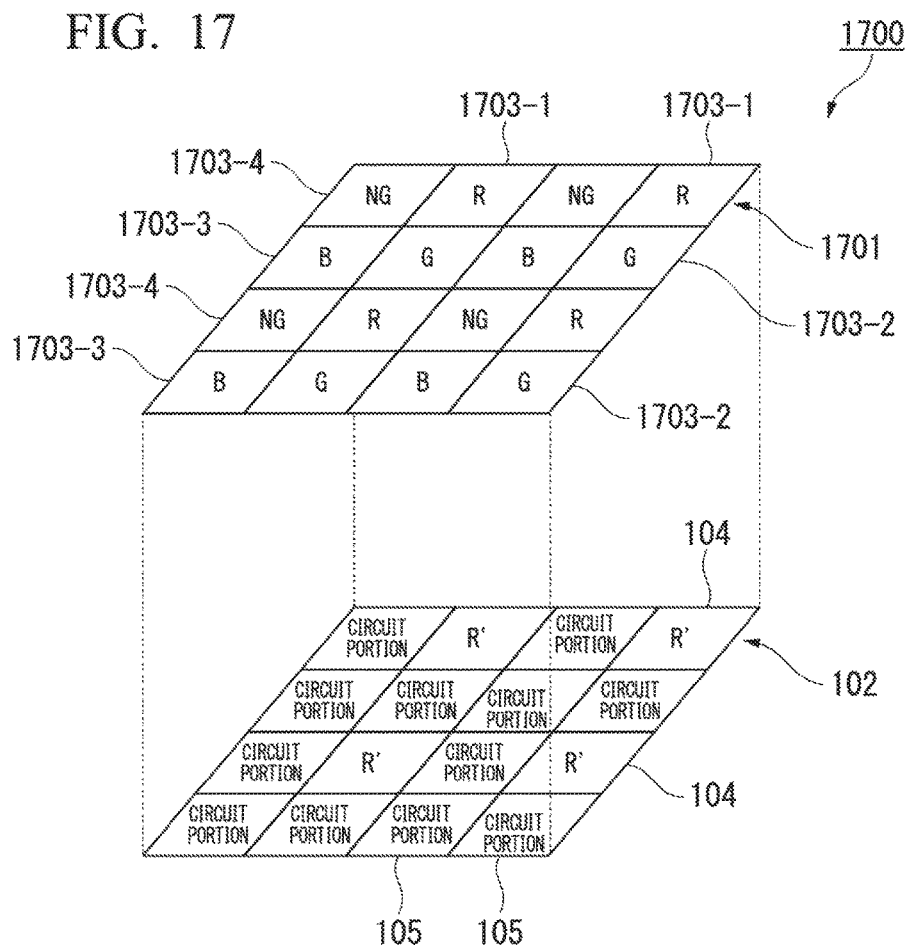
FIG. 17 is a schematic diagram which shows an arrangement of a first pixel, a second pixel, and a circuit portion according to a fifth embodiment of the present invention.

Next, the arrangement of the first pixels 1703, the second pixels 104, and the circuit portions 105 will be described. FIG. 17 is a schematic diagram which shows the arrangement of the first pixels 1703, the second pixels 104, and the circuit portions 105 in the present embodiment. In an example shown in FIG. 17, sixteen first pixels 1703 regularly arranged in a two-dimensional shape of four rows and four columns are included in the first substrate 1701. Four second pixels 104 and twelve circuit portions 105 regularly arranged in the two-dimensional shape of four rows and four columns are included in the second substrate 102.

As shown in FIG. 17, the first pixels 1703-4 (NG pixels), instead of some G pixels in the Bayer arrangement, are arranged in the first substrate 1701. Specifically, the first pixels 1703-4 (NG pixels), instead of G pixels in the Bayer arrangement, are arranged in the first and third columns of the first substrate 1701. The first pixels 1703-2 (G pixels) are arranged in the second and fourth columns of the first substrate 1701. An arrangement of the first pixels 1703-1 (R pixels) and the first pixels 1703-3 (B pixels) is the same as the Bayer arrangement.

Incident light is directly incident on the first pixels 1703-1 to 1703-4. As a result, it is possible to output the first signal (R signal) in accordance with an exposure amount of red light among the incident light, the second signal (G signal) in accordance with an exposure amount of green light among the incident light, the third signal (B signal) in accordance with an exposure amount of blue light among the incident light, and the fifth signal (NG signal, a narrow green signal) in accordance with an exposure amount of the light having a peak wavelength of 540 nm (green light) among the incident light in the first substrate 1701.

As shown in FIG. 17, the second pixels 104 are arranged at positions corresponding to the first pixels 1703-1 (for example, positions immediately under the first pixels 1703-1) in the second substrate 102. Moreover, the circuit portions 105 are arranged at positions corresponding to the first pixels 1703-2 to 1703-4 (for example, positions immediately under the first pixels 1703-2 to 1703-4) in the second substrate 102.

With such an arrangement, light which has passed through the first pixel 1703-1 of the first substrate 1701 among the incident light is incident on the second pixels 104. The color filter 1723-1 included in the first pixels 1703-1 transmit the light having a peak wavelength of 600 nm (red light). Moreover, the first substrate 1701 is a silicon substrate and transmits light in a wavelength band including the wavelength of red light. Therefore, the light having a peak wavelength of 600 nm (red light) among the incident light is incident on the second pixels 104 of the second substrate 102.

Therefore, even if the first pixels 1703-1 of the first substrate 1701 are present on the light-receiving surface sides of the second pixels 104 of the second substrate 102, the second pixels 104 can output the fourth signal (R' signal, a red' signal) in accordance with an exposure amount of the light having a peak wavelength of 630 nm (red light) among the incident light.

The color filters 1723-2 included in the first pixels 1703-2 transmit only the light having a peak wavelength of 540 nm (green light). That is, the color filters 1723-2 do not transmit red light. The color filters 1723-3 included in the first pixels 1703-3 transmit only the light having a peak wavelength of 460 nm (blue light). That is, the color filters 1723-3 do not transmit red light. The Fabry-Perot filters 825 included in the first pixels 1703-4 transmit only the light having a peak wavelength of 540 nm (green light). That is, the Fabry-Perot filters 825 do not transmit red light. Therefore, light which has passed through the first pixels 1703-2 to 1703-4 does not include red light.

Accordingly, even if the second pixels 104 are arranged under the first pixels 1703-2 to 1703-4, it is difficult to accurately detect the light having a peak wavelength of 630 nm (red light). For example, if various types of circuits are arranged around the first pixels 1703 and the second pixels 104, it is considered that the aperture ratios of the first pixels 1703 and the second pixels 104 decrease and S/N ratios of the first to fifth signals decrease.

In the present embodiment, various types of circuits are arranged as the circuit portions 105 under the first pixels 1703-2 (G pixels), the first pixels 1703-3 (B pixels), and the first pixels 1703-4 (NG pixels) which are difficult to transmit the light having a peak wavelength of 630 nm (red light), and thereby the aperture ratios of the first pixels 1703-1 to 1703-4 and the second pixels 104 can increase. Accordingly, it is possible to increase the S/N ratios of the first to third, and fifth signals output by the first pixels 1703-1 to 1703-4.

Moreover, it is possible to increase the S/N ratio of the fourth signal output by the second pixels.

The number and arrangement of the first pixels 1703-1 to 1703-4 included in the first substrate 1701, and the second pixels 104 and the circuit portions 105 included in the second substrate 102 are not limited to the example shown in FIG. 17, and may be any number and arrangement. In the example shown in FIG. 17, the second pixels 104 are arranged under the first pixels 1703-1 in a corresponding manner, but the present embodiment is not limited thereto. For example, it is possible to devise such a method that a pixel size of the second pixel 104 is set to a size different from a pixel size of the first pixel 1703-1 (for example, an integral multiple of the first pixel 1703-1). For example, it is possible to devise such a method that a size of the circuit portion 105 is set to a size different from pixel sizes of the first pixels 1703-2 to 1703-4.

Since the first pixels 1703-1 to 1703-4 and the second pixels 104 are irradiated with incident light at the same time due to the arrangement of the first pixels 1703-1 to 1703-4 and the second pixels 104 described above, it is possible to simultaneously output the first signal (R signal), the second signal (G signal), the third signal (B signal), the fourth signal (R' signal), and the fifth signal (NG signal) at the same time. As a result, a positional deviation can be prevented from occurring in images of each wavelength.

The configuration and the operation of an imaging device including the imaging element 1700 are the same as those of the imaging device 1 in the first embodiment. For example, an image processing method by the spectroscopic signal generation unit 501 is the same method as in the first embodiment. In the present embodiment, the fifth signal (NG signal) output by the first pixels 1703-4 can be obtained, it is possible to improve an image quality by using the fifth signal (NG signal) for image processing.

As described above, according to the present embodiment, the first substrate 1701 and the second substrate 102 are stacked. The second substrate 102 is disposed at a position overlapping the first substrate 1701 and on a side opposite to a light-receiving surface side of the first substrate 1701 as seen from the light-receiving surface of the first substrate 1701. The first substrate 1701 transmits light. Moreover, the second substrate 102 is irradiated with the light which has passed through the first substrate 1701.

As a result, it is possible to expose the first pixels 1703 of the first substrate 1701 and the second pixels 104 of the second substrate 102 at the same time. That is, generations of the first signal (R signal) by the first pixels 1703-1, the second signal (G signal) by the first pixels 1703-2, the third signal (B signal) by the first pixels 1703-3, the fifth signal (NG signal) by the first pixels 1703-4, and the fourth signal (R' signal) by the second pixels 104 can be performed at the same time. Accordingly, a deviation in imaging timing of each wavelength can be prevented from occurring. This enables the spectroscopic signal generation unit 501 to generate images such that a positional deviation of each wavelength does not occur. Therefore, for example, when an image generated by the spectroscopic signal generation unit 501 is an image that emphasizes a blood vessel, an accurate position of the blood vessel can be known.

(Sixth Embodiment)

Next, a sixth embodiment of the present invention will be described. A difference between an imaging device of the present embodiment and the imaging device 1 of the first embodiment is the configuration of the imaging element. The imaging element 100 of the first embodiment and an imaging element 1800 of the present embodiment have different types of light detected by first pixels 1803 included in a first substrate 1801 and different types of light detected by the second pixel 1804 included in a second substrate 1802. An arrangement of the first pixels 1803 in the first substrate 1801 and an arrangement of second pixels 1804 in the second substrate 1802 are different between these imaging elements. The other configurations are the same as in the first embodiment.

The imaging element 1800 includes the first substrate 1801, the second substrate 1802, a plurality of first pixels 1803, a plurality of second pixels 1804, and the plurality of circuit portions 105. A side irradiated with incident light is set to a light-receiving surface.

The first substrate 1801 and the second substrate 1802 are stacked. The first substrate 1801 and the second substrate 1802 are silicon substrates. The first substrate 1801 transmits a portion of incident light.

The first pixels 1803 are arranged in the first substrate 1801. Among the first pixels 1803, a first pixel 1803-1 includes a first photodiode 1813-1 for detecting light, and a color filter 1823-1 for transmitting the light having a peak wavelength of 600 nm (red light). As a result, the first pixel 1803-1 outputs the first signal (R signal, a red signal) in accordance with an exposure amount of the light having a peak wavelength of 600 nm (red light) among the incident light. Hereinafter, the first pixel 1803-1 is referred to as an R pixel.

Among the first pixels 1803, a first pixel 1803-2 includes a first photodiode 1813-2 for detecting light and a color filter 1823-2 for transmitting the light having a peak wavelength of 540 nm (green light). As a result, the first pixel 1803-2 outputs the second signal (G signal, a green signal) in accordance with an exposure amount of the light having a peak wavelength of 540 nm (green light) among the incident light. Hereinafter, the first, pixel 1803-2 is referred to as a G pixel.

Among the first pixels 1803, a first pixel 1803-3 includes a first photodiode 1813-3 for detecting light and a color filter 1823-3 for transmitting the light having a peak wavelength of 460 nm (blue light). As a result, the first pixel 1803-3 outputs the third signal (B signal, a blue signal) in accordance with an exposure amount of the light having a peak wavelength of 460 nm (blue light) among the incident light. Hereinafter, the first pixel 1803-3 is referred to as a B pixel.

Among the first pixels 1803, a first pixel 1803-4 includes a first photodiode 1813-4 for detecting light and the Fabry-Perot filter 825 for transmitting the light in a narrow band having a peak wavelength of 540 nm (green light). As a result, the first pixel 1803-4 outputs the fifth signal (NG signal, a narrow green signal) in accordance with an exposure amount of the light in a narrow band having a peak wavelength of 540 nm (green light) among the incident light. Hereinafter, the first pixel 1803-4 is referred to as an NG pixel.

The second pixels 1804 and the circuit portions 105 are arranged in the second substrate 1802. The configuration of the circuit portions 105 is the same as in the first embodiment. The circuit portions 105 include various types of circuits.

Among the second pixels 1804, a second pixel 1804-1 includes a second photodiode 1814-1 for detecting light and the Fabry-Perot filter 1824-1 for transmitting the light in a narrow band having a peak wavelength of 600 nm (red light). As a result, the second pixel 1804-1 outputs the eleventh signal (NR1 signal, a narrow red 1 signal) in accordance with an exposure amount of the light in a narrow band having a peak wavelength of 600 nm (red light) among the incident light. Hereinafter, the second pixel 1804-1 is referred to as an NR1 pixel.

Among the second pixels 1804, a second pixel 1804-2 includes a second photodiode 1814-2 for detecting light and the Fabry-Perot filter 1824-2 for transmitting the light in a narrow band having a peak wavelength of 630 nm (red light). As a result, the second pixel 1804-2 outputs the twelfth signal (NR2 signal, a narrow red 2 signal) in accordance with an exposure amount of the light in a narrow band having a peak wavelength of 630 nm (red light) among the incident light. Hereinafter, the second pixel 1804-2 is referred to as an NR2 pixel.

The Fabry-Perot filter 1824-1 transmitting the light in a narrow band having a peak wavelength of 600 nm (red light) can be realized by, for example, superimposing an R filter and a Ye filter in an on-chip color filter of an organic pigment image sensor. Moreover, the Fabry-Perot filter 1824-2 transmitting the light in a narrow band having a peak wavelength of 630 nm (red light) can be realized by, for example, superimposing the Ye filter and a V (violet) filter in the on-chip color filter of an organic pigment image sensor.

Figure 18:
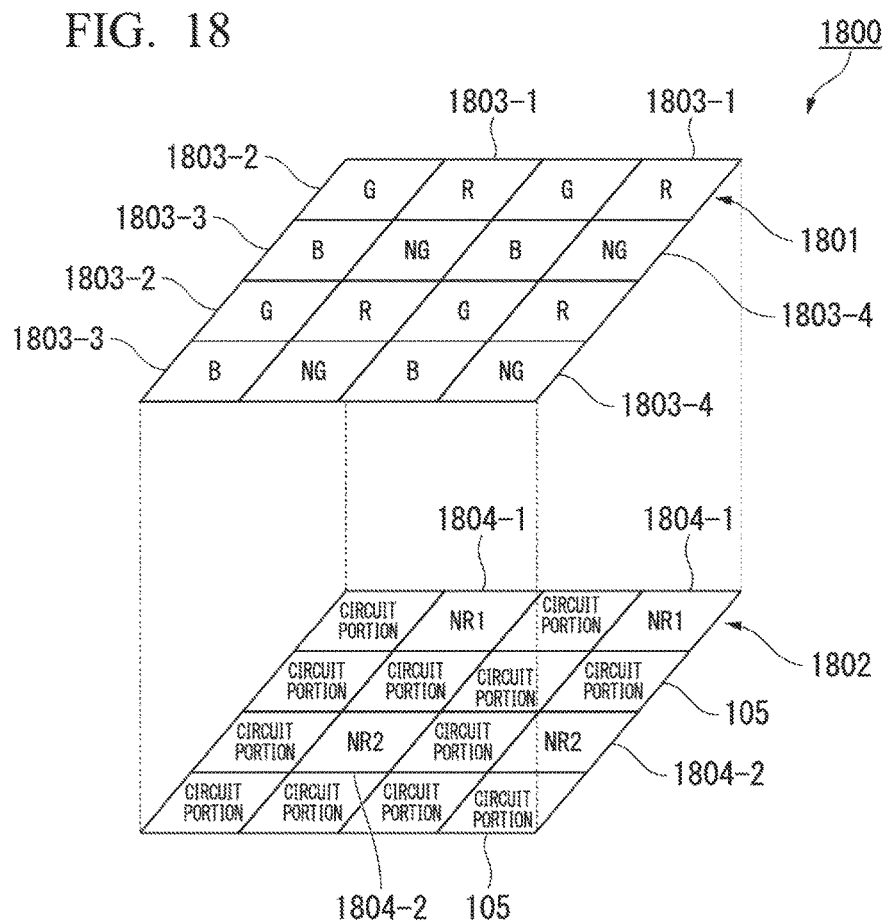
FIG. 18 is a schematic diagram which shows an arrangement of a first pixel a second pixel, and a circuit portion according to a sixth embodiment of the present invention.

Next, the arrangement of the first pixels 1803, the second pixels 1804, and the circuit portions 105 will be described. FIG. 18 is a schematic diagram which shows the arrangement of the first pixels 1803, the second pixels 1804, and the circuit portions 105 in the present embodiment. In an example shown in FIG. 18, sixteen first pixels 1803 regularly arranged in a two-dimensional shape of four rows and four columns are included in the first substrate 1801. Four second pixels 1804 and twelve circuit portions 105 regularly arranged in the two-dimensional shape of four rows and four columns are included in the second substrate 1802.

As shown in FIG. 18, the first pixels 1803-4 (NG pixels), instead of some G pixels in the Bayer arrangement, are arranged in the first substrate 1801. Specifically, the first pixels 1803-4 (NG pixels), instead of G pixels in the Bayer arrangement, are arranged in the second and fourth columns of the first substrate 1801. The first pixels 1803-2 (G pixels) are arranged in the same manner as the Bayer arrangement in the first and third columns of the first substrate 1801. An arrangement of the first pixels 1803-1 (R pixels) and the first pixels 1803-3 (B pixels) is the same as the Bayer arrangement.

Incident light is directly incident on the first pixels 1803-1 to 1803-4. As a result, it is possible to output the first signal (R signal) in accordance with an exposure amount of red light among the incident light, the second signal (G signal) in accordance with an exposure amount of green light among the incident light, the third signal (B signal) in accordance with an exposure amount of blue light among the incident light, and the fifth signal (NG signal, a narrow green signal) in accordance with an exposure amount of the light having a peak wavelength of 540 nm (green light) among the incident light in the first substrate 1801.

As shown in FIG. 13, the second pixels 1804-1 or the second pixels 1804-2 are arranged at positions corresponding to the first pixels 1803-1 (for example, positions immediately under the first pixels 1803-1) in the second substrate 1802. Specifically, the second pixels 1804-1 (NR1 pixels) are arranged in the first row of the second substrate 1802 among the positions corresponding to the first pixels 1803-1. Moreover, the second pixels 1804-2 (NR2 pixels) are arranged in the third row of the second substrate 1802 among the positions corresponding to the first pixels 1803-1.

The circuit portions 105 are arranged at positions corresponding to the first pixels 1803-2 to 1803-4 (for example, positions immediately under the first pixels 1803-2 to 1803-4).

With such an arrangement, light which has passed through the first pixels 1803-1 of the first substrate 1801 among the incident light is incident on the second pixels 1804. The color filters 1823-1 included in the first pixels 1803-1 transmit the light having a peak wavelength of 600 nm (red light). Moreover, the first substrate 1801 is a silicon substrate and transmits light in a wavelength band including the wavelength of red light. Therefore, the light having a peak wavelength of 600 nm (red light) among the incident light is incident on the second pixels 1804 of the second substrate 1802.

Therefore, even if the first pixels 1803-1 of the first substrate 1801 are present on the light-receiving surface sides of the second pixels 1804 of the second substrate 1802, the second pixels 1804-1 can output the eleventh signal (NR1 signal, a narrow red 1 signal) in accordance with an exposure amount of the light in a narrow band having a peak wavelength of 600 nm (red light) among the incident light. The second pixels 1804-2 can output the twelfth signal (NR2 signal, a narrow red 2 signal) in accordance with an exposure amount of the light in a narrow band having a peak wavelength of 630 nm (red light) among the incident light.

The color filters 1823-2 included in the first pixels 1803-2 transmit only the light having a peak wavelength of 540 nm (green light). That is, the color filters 1823-2 do not transmit red light. The color filters 1823-3 included in the first pixels 1803-3 transmit only the light having a peak wavelength of 460 nm (blue light). That is, the color filters 1823-3 do not transmit red light. The Fabry-Perot filters 825 included in the first pixels 1803-4 transmit only the light having a peak wavelength of 540 nm (green light). That is, the Fabry-Perot filters 825 do not transmit red light. Therefore, light which has passed through the first pixels 1803-2 to 1803-4 does not include red light.

Accordingly, even if the second pixels 1804-1 are arranged under the first pixels 1803-2 to 1803-4, it is difficult to accurately detect the light having a peak wavelength of 600 nm (red light). Even if the second pixels 1804-2 are arranged under the first pixels 1803-2 to 1803-4, it is difficult to accurately detect the light having a peak wavelength of 630 nm (red light). For example, if various types of circuits are arranged around the first pixels 1803 and the second pixels 1804, it is considered that the aperture ratios of the first pixels 1803 and the second pixels 1804 decrease and S/N ratios of the first to third, fifth, eleventh, and twelfth signals decrease.

In the present embodiment, various types of circuits are arranged as the circuit portions 105 under the first pixels 1803-2 (G pixels), the first pixels 1803-3 (B pixels), and the first pixels 1803-4 (NG pixels) which are difficult to transmit the light having a peak wavelength of 600 nm or 630 nm (red light), and thereby the aperture ratios of the first pixels 1803-1 to 1803-4 and the second pixels 1804 can increase. Accordingly, it is possible to increase the S/N ratios of the first to third, and fifth signals output by the first pixels 1803-1 to 1803-4. Moreover, it is possible to increase the S/N ratio of the eleventh and twelfth signals output by the second pixels.

The number and arrangement of the first pixels 1303-1 to 1803-4 included in the first substrate 1801, and the second pixels 1804-1 and 1804-2 and the circuit portions 105 included in the second substrate 1802 are not limited to the example shown in FIG. 18, and may be any number and arrangement. In the example shown in FIG. 18, the second pixels 1804-1 or 1804-2 are arranged under the first pixels 1803-1 in a corresponding manner, but the present embodiment is not limited thereto. For example, it is possible to devise such a method that a pixel size of the second pixel 1804-1 or the second pixel 1804-2 is set to a size different from a pixel size of the first pixel 1803-1 (for example, an integral multiple of the first pixel 1803-1). For example, it is possible to devise such a method that a size of the circuit portion 105 is set to a size different from pixel sizes of the first pixels 1803-2 to 1803-4.

Since the first pixels 1803-1 to 1803-4 and the second pixels 1804-1 and 18:04-2 are irradiated with incident light at the same time due to the arrangement of the first pixels 1803-1 to 1803-4 and the second pixels 1804-1 and 1804-2 described above, it is possible to simultaneously output the first signal (R signal), the second signal (G signal), the third signal (B signal), the fifth signal (NG signal), the eleventh signal (NR1 signal), and the twelfth signal (NR2 signal) at the same time. As a result, a positional deviation can be prevented from occurring in images of each wavelength.

A configuration and an operation of an imaging device including the imaging element 1800 are the same as those of the imaging device 1 in the first embodiment. For example, an image processing method by the spectroscopic signal generation unit 501 is the same method as in the first embodiment.

In the present embodiment, the fifth signal (NG signal) output by the first pixels 1804-4, the eleventh signal (NR1 signal) output by the second pixels 1804-1, and the twelfth signal (NR2 signal) output by the second pixels 1804-2 can be obtained, it is possible to improve an image quality by using the fifth signal (NG signal), the twelfth signal (NR1 signal), and the twelfth signal (NR2 signal) for image processing.

Specifically, the spectroscopic signal generation unit 501 can perform emphasis processing of thick blood vessels of interest with higher accuracy by generating wavelength images corresponding to wavelengths of λ1'=NG signal, λ2'=NR1 signal, λ3=NR2 signal, performing image processing using the generated wavelength images, and performing emphasis processing on thick blood vessels.

As described above, according to the present embodiment, the first substrate 1801 and the second substrate 1802 are stacked. The second substrate 1802 is disposed at a position overlapping the first substrate 1801 and on a side opposite to a light-receiving surface side of the first substrate 1801 as seen from the light-receiving surface of the first substrate 1801. The first substrate 1801 transmits light. Moreover, the second substrate 1802 is irradiated with the light which has passed through the first substrate 1801.

As a result, it is possible to expose the first pixels 1803 of the first substrate 1801 and the second pixels 1804 of the second substrate 1802 at the same time. That is, generations of the first signal (R signal) by the first pixels 1803-1, the second signal (G signal) by the first pixels 1803-2, the third signal (B signal) by the first pixels 1803-3, the fifth signal (NG signal) by the first pixels 1803-4, the eleventh signal (NR1 signal) by the second pixels 1804-1, and the twelfth signal (NR2 signal) by the second pixels 1804-2 can be performed at the same time. Accordingly, a deviation in imaging timing of each wavelength can be prevented from occurring. This enables the spectroscopic signal generation unit 501 to generate images such that a positional deviation of each wavelength does not occur. Therefore, for example, when an image generated by the spectroscopic signal generation unit 501 is an image that emphasizes a blood vessel, an accurate position of the blood vessel can be known.

(Seventh Embodiment)

Next, a seventh embodiment of the present invention will be described. In the present embodiment, an endoscope device 3000 which includes an imaging device equipped with any one of the imaging elements 100, 800, 1100, 1500, 1700, and 1800 described in the first to sixth embodiments will be described.

Figure 19:
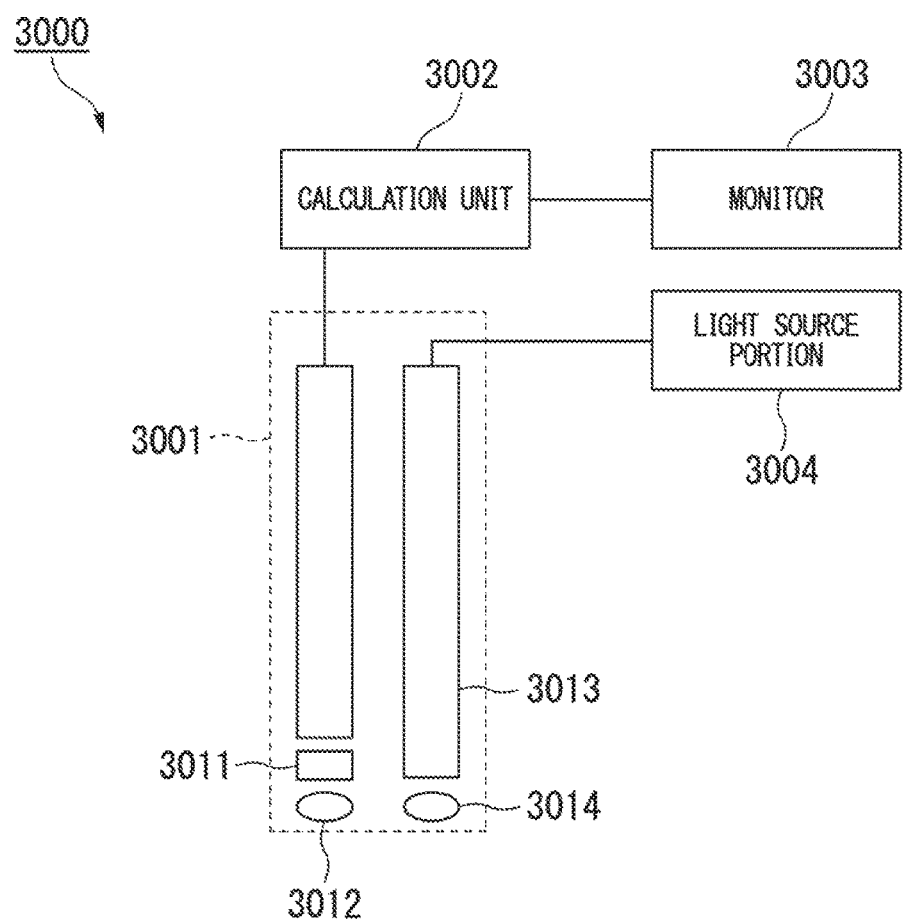
FIG. 19 is a block diagram which shows a configuration of an endoscope device according to a seventh embodiment of the present invention.

FIG. 19 is a block diagram which shows a configuration of the endoscope device 3000 according to the present embodiment. In an example shown, the endoscope device 3000 includes an endoscope scope 3001, a calculation unit 3002, a monitor 3003, and a light source portion 3004. The calculation unit 3002 performs control on all units of the endoscope device 3000. The monitor 3003 is, for example, a liquid crystal display, and displays images. The light source portion 3004 is, for example, an LED, and emits white light illumination light.

The endoscope scope 3001 includes an imaging device 3011, an imaging lens 3012, a light guide 3013, and an illumination lens 3014. The imaging device 3011 is equipped with any one of the imaging elements 100, 300, 1100, 1500, 1700, and 1800 described in the first to sixth embodiments. The imaging device 3011 is disposed at a tip of the endoscope scope 3001. The imaging lens 3012 is disposed on a light-receiving surface side of the imaging element included in the imaging device 3011. Moreover, the illumination lens 3014 is disposed at the tip of the endoscope scope 3001.

The light guide 3013 irradiates the illumination lens 3014 with the light emitted by the light source portion 3004. The illumination lens 3014 collects the light emitted from the light guide 3013 and irradiates a subject with the light. The imaging lens 3012 collects light from the subject and irradiates the imaging element included in the imaging device 3011.

The imaging device 3011 generates images according to the light emitted by the imaging lens 3012. That is, the imaging device 3011 images returning light of illumination light emitted to the subject from the light source portion 3004. A method of generating an image is the same as methods described in the first to sixth embodiments. The calculation unit 3002 displays images generated by the imaging device 3011 on the monitor 3003.

For example, the imaging device 3011 including any one of the imaging elements 100, 800, 1100, 1500, 1700, and 1800 described in the first to sixth embodiments can prevent a positional deviation from occurring in images of each wavelength. Therefore, it is possible to prevent a positional deviation from occurring in images of each wavelength by using the imaging device 3011 including any one of the imaging elements 100, 800, 1100, 1500, 1700, and 1800 described in the first to sixth embodiments in the endoscope device 3000.

It is possible to detect light corresponding to a central wavelength 600 nm or 630 nm, and to generate a signal in accordance with an intensity of the detected light. Moreover it is possible to observe a state of a thick blood vessel more clearly by performing emphasis processing on an image using the generated signal.

Although preferred embodiments of the present invention have been described above, the present invention is not limited to the embodiments and modifications thereof. Additions, omissions, substitutions and other changes in the structure are possible without departing from the spirit of the present invention. The present invention is not limited by the foregoing description but is limited only by the scope of the appended claims.

What is claimed is:

1. An imaging device comprising:
   a first substrate which includes a pixel array having a plurality of first pixels;
   a second substrate which is disposed to be stacked with the first substrate on a side opposite to a light-receiving surface of the pixel array;
   a filter configured to narrow a band of light of a first wavelength to a predetermined wavelength band, the light of the first wavelength having passed through the first substrate;
   a plurality of second pixels which are included in the second substrate, the plurality of second pixels receiving light whose band is narrowed by the filter; and
   a spectroscopic signal generation circuit configured to generate a spectroscopic signal by using pixel signals output from the first pixels and the second pixels according to the light received by the first pixels and the second pixels,
   wherein the filter is configured by a first Fabry-Perot filter or a second Fabry-Perot filter according to a position of each of the second pixels,
   wherein the first Fabry-Perot filter and the second Fabry-Perot filter have different transmission wavelength bands,
   wherein a peak wavelength of the transmission wavelength band of the first Fabry-Perot filter is narrow band light in the vicinity of 600 nm,
   wherein a peak wavelength of the transmission wavelength band of the second Fabry-Perot filter is narrow band light in the vicinity of 630 nm, and
   wherein the spectroscopic signal generation circuit generates a spectroscopic signal according to a difference between a pixel signal output from the first pixels and a pixel signal output from the second pixels, the spectroscopic signal being different from the pixel signals output from each of the first pixels and the second pixels.

2. The imaging device according to claim 1,
   wherein the first pixels include an R pixel for detecting red light, a G pixel for detecting green light, and a B pixel for detecting blue light, and
   wherein the filter and the second pixels are arranged in the second substrate to receive light which has passed through the R pixel among the plurality of first pixels.

3. The imaging device according to claim 1, further comprising:
   a second filter which narrows a band of light which has passed through a G pixel for detecting green light among the first pixels to a predetermined wavelength band; and a plurality of third pixels which are included in the second substrate and receive light whose band is narrowed by the second filter,
   wherein the first pixels includes an R pixel for detecting red light, a G pixel for detecting green light, and a B pixel for detecting blue light, and
   wherein the second filter and the third pixels are arranged in the second substrate to receive light which has passed through the G pixel among the plurality of first pixels.

4. The imaging device according to claim 1,
   wherein the first pixels include a C pixel for detecting cyan light, an M pixel for detecting magenta light, and a Y pixel for detecting yellow light, and
   wherein the filter and the second pixels are arranged in the second substrate to receive light which has passed through the M pixel or the Y pixel among the plurality of first pixels.

5. The imaging device according to claim 1,
   wherein one or more first pixels are clear pixels, and
   wherein the filter and the second pixels are arranged in the second substrate such that the filter and the second pixels receive light which has passed through the clear pixels among the plurality of first pixels.

6. The imaging device according to claim 1,
   wherein one or more first pixels are pixels configured to detect narrow band light whose wavelength is in the vicinity of 540 nm.

7. An endoscope device comprising:
   a light source configured to emit white illumination light to a subject; and
   an imaging device configured to image returning light of the illumination light emitted to the subject from the light source,
   wherein the imaging device includes:
   a first substrate which includes a pixel array having a plurality of first pixels;
   a second substrate which is disposed to be stacked with the first substrate on a side opposite to a light-receiving surface of the pixel array;
   a filter configured to narrow a band of light of a first wavelength band to a predetermined wavelength band, the light of the first wavelength having passed through the first substrate;
   a plurality of second pixels which are included in the second substrate and receive light whose band is narrowed by the filter; and
   a spectroscopic signal generation circuit configured to generate a spectroscopic signal by using pixel signals output from the first pixels and the second pixels according to the light received by the first pixels and the second pixels,
   wherein the filter is configured by a first Fabry-Perot filter or a second Fabry-Perot filter according to a position of each of the second pixels,
   wherein the first Fabry-Perot filter and the second Fabry-Perot filter have different transmission wavelength bands,
   wherein a peak wavelength of the transmission wavelength band of the first Fabry-Perot filter is narrow band light in the vicinity of 600 nm,
   wherein a peak wavelength of the transmission wavelength band of the second Fabry-Perot filter is narrow band light in the vicinity of 630 nm, and
   wherein the spectroscopic signal generation circuit generates a spectroscopic signal according to a difference between a pixel signal output from the first pixels and a pixel signal output from the second pixels, the spectroscopic signal being different from the pixel signals output from each of the first pixels and the second pixels.

* * * * *